US010577617B2

(12) United States Patent
Grennan et al.

(10) Patent No.: US 10,577,617 B2
(45) Date of Patent: Mar. 3, 2020

(54) PLANTS HAVING INCREASED BIOMASS AND METHODS FOR MAKING THE SAME

(71) Applicants: The Board of Trustees of the University of Illinois, Urbana, IL (US); The United States of America, as represented by the Secretary of Agriculture, Washington, DC (US); The Board of Regents of the University of Nebraska, Lincoln, NE (US); The University of Florida Research Foundation, Incorporated, Gainesville, FL (US)

(72) Inventors: Aleel K. Grennan, Urbana, IL (US); Donald R. Ort, Champaign, IL (US); Stephen Patrick Moose, Urbana, IL (US); Damla D. Bilgin, San Diego, CA (US); Thomas Clemente, Lincoln, NE (US); Fredy Altpeter, Gainesville, FL (US); Stephen P. Long, Champaign, IL (US)

(73) Assignees: The Board of Trustees of the University of Illinois, Urbana, IL (US); The United States of America, as Represented by the Secretary of Agriculture, Washington, DC (US); The Board of Regents of the University of Nebraska, Lincoln, NE (US); The University of Florida Research Foundation, Incorporated, Gainesville, FL (US)

( * ) Notice: Subject to any disclaimer, the term of this patent is extended or adjusted under 35 U.S.C. 154(b) by 451 days.

(21) Appl. No.: 14/995,109

(22) Filed: Jan. 13, 2016

(65) Prior Publication Data
US 2016/0289694 A1  Oct. 6, 2016

Related U.S. Application Data

(60) Provisional application No. 62/102,783, filed on Jan. 13, 2015.

(51) Int. Cl.
*C12N 15/82* (2006.01)

(52) U.S. Cl.
CPC ..... *C12N 15/8218* (2013.01); *C12N 15/8261* (2013.01)

(58) Field of Classification Search
None
See application file for complete search history.

(56) References Cited

U.S. PATENT DOCUMENTS

2011/0305718 A1* 12/2011 Ludevid M gica .. C07K 14/415
424/184.1

FOREIGN PATENT DOCUMENTS

WO  WO 0032799 A1 *  6/2000

OTHER PUBLICATIONS

Niu et al. (Journal of Experimental Botany, vol. 68, No. 21-22 pp. 5773-5786, 2017). (Year: 2017).*
Hudson et al. (Plant physiology (2013): vol. 162, pp. 132-144). (Year: 2013).*
Dong et al. (Acta Botanica Sinica 2002, 44 (7) :838-844). (Year: 2002).*
GenBank Accession CA101907, dated Feb. 1, 2011. (Year: 2011).*
Helliwell et al. (Methods in enzymology. vol. 392. Academic Press, 2005. 24-35). (Year: 2005).*
Pyke (American Journal of Botany 84(9): 1017-1027.1997). (Year: 1997).*
Martin et al. (Molecular plant 2.6 (2009):1359-1372). (Year: 2009).*
Fouad et al., "Altering lignin content in bahia grass (*Paspalum notatum* Flugge) by downregulation of 4-coumarate-CoA ligase." In: In Vitro *Biology Meeting and IAPB 12th World Congress Abstract Issue*, In Vitro *Cell. Dev. Biol.—Animal* 46 (Suppl 1):S114-S115, P-052, 2010 (DOI 10.1007/s11626-010-9339-6).
Hudson et al., "Rice Cytokinin GATA Transcription Factor1 Regulates Chloroplast Development and Plant Architecture," *Plant Physiol*, 162:132-144, 2013.
Koslowsky et al., "Higher biomass accumulation by increasing phosphoribosylpyrophosphate synthetase activity in *Arabidopsis thaliana* and *Nicotiana tabacum*," *Plant Biotechnology Journal*, 6:281-294, 2008.
Martin et al., "Targeted Gene Knockouts Reveal Overlapping Functions of the Five *Physcomitrella patens* FtsZ Isoforms in Chloroplast Division, Chloroplast Shaping, Cell Patterning, Plant Development, and Gravity Sensing," *Molecular Plant*, 2(6):1359-1372, 2009.
Osteryoung et al., "Chloroplast Division in Higher Plants Requires Members of Two Functionally Divergent Gene Families with Homology to Bacterial ftsZ," *The Plant Cell*, 10:1991-2004, 1998.
Osteryoung & Vierling, "Conserved cell and organelle division," *Nature*, 376:473-474, 1995.
Pyke "Plastid division," *AoB Plants* 2010: plq016, doi:10.1093/aobpla/plq016.
Rensing et al., "Diversification of ftsZ during early land plant evolution," *Journal of Molecular Evolution*, 58(2):154-162, 2004.
Strepp et al., "Plant nuclear gene knockout reveals a role in plastid division for the homolog of the bacterial cell division protein FtsZ, an ancestral tubulin." *Proc. Natl. Acad. Sci. USA*, 95:4368-4373, 1998.

(Continued)

*Primary Examiner* — Charles Logsdon
(74) *Attorney, Agent, or Firm* — Klarquist Sparkman LLP

(57) ABSTRACT

The impact of plastid size change in both monocot and dicot plants has been examined. In both, when plastid size is increased there is an increase in biomass relative to the parental lines. Thus, provided herein are methods for increasing the biomass of a plant, comprising decreasing the expression of at least one plastid division protein in a plant. Optionally, the level of chlorophyll in the plant is also reduced.

7 Claims, 22 Drawing Sheets
(7 of 22 Drawing Sheet(s) Filed in Color)
Specification includes a Sequence Listing.

(56) References Cited

OTHER PUBLICATIONS

Taparia et al., "Rapid production of transgenic sugarcane with the introduction of simple loci following biolistic transfer of a minimal expression cassette and direct embryogenesis." In Vitro *Cell. Dev. Biol.-Plant*, 48:15-22, 2010.

Warnasooriya et al., "Enhancing the productivity of grasses under high-density planting by engineering light responses: from model systems to feedstocks," *Journal of Experimental Botany*, 65(11):2825-2834, 2014.

Yoder et al., "Effects of mutations in Arabidopsis FtsZ1 on plastid division, FtsZ ring formation and positioning, and FtsZ filament morphology in vivo." *Plant Cell Physiol.*, 48:775-791, 2007.

\* cited by examiner

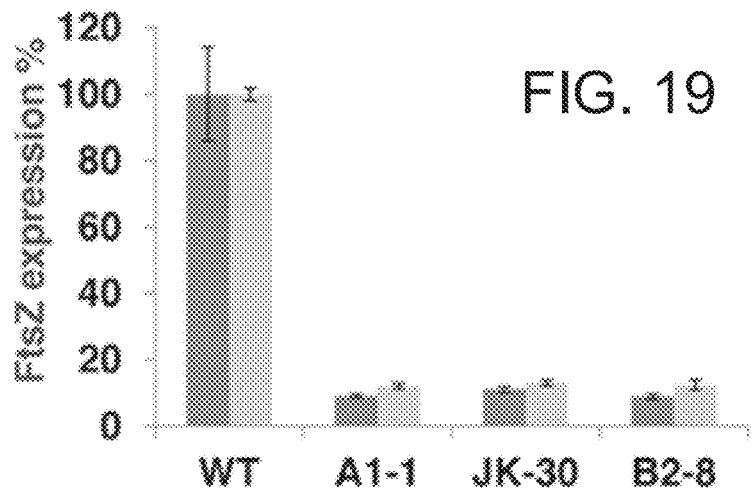
FIG. 19
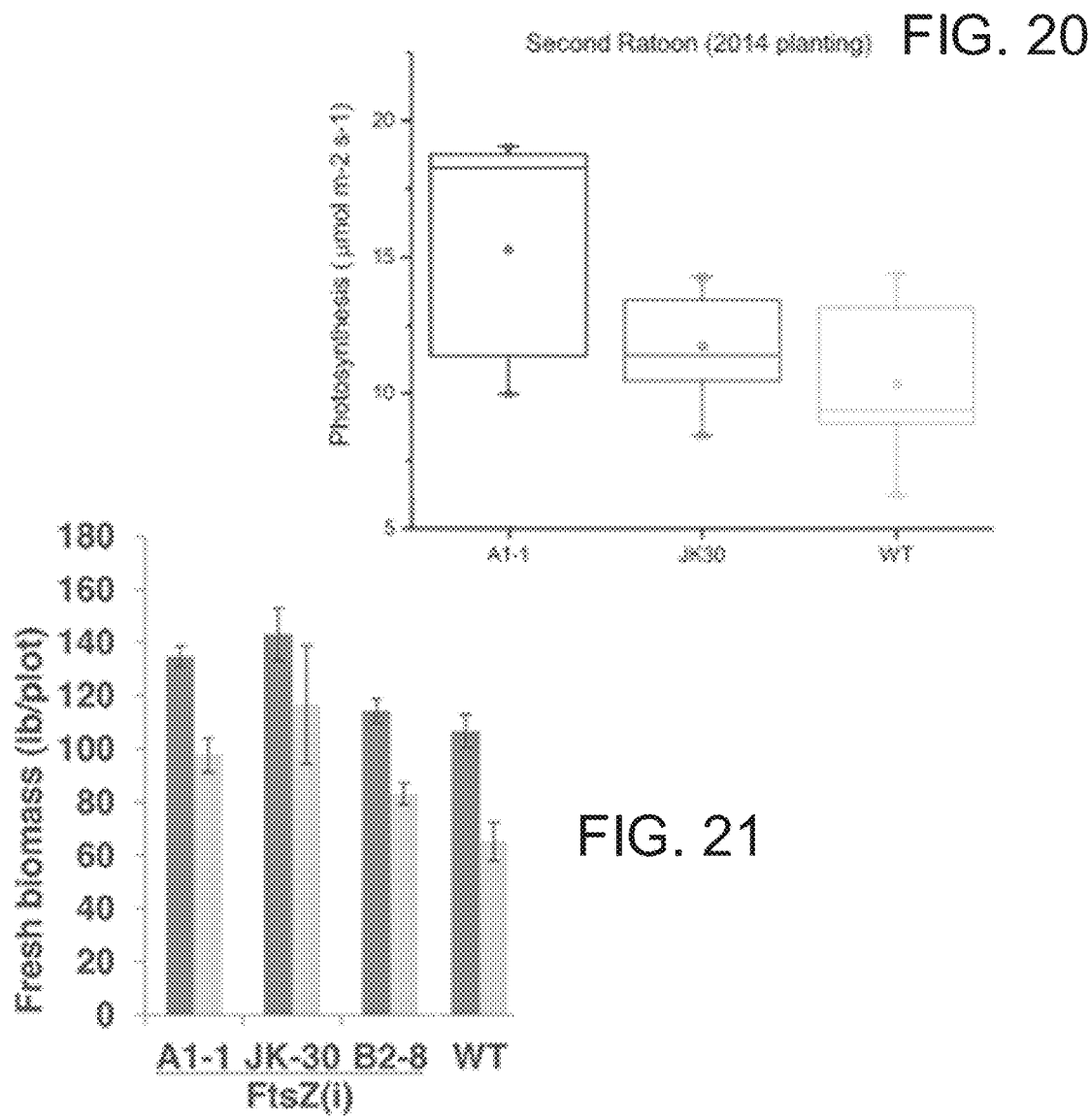
FIG. 20
FIG. 21

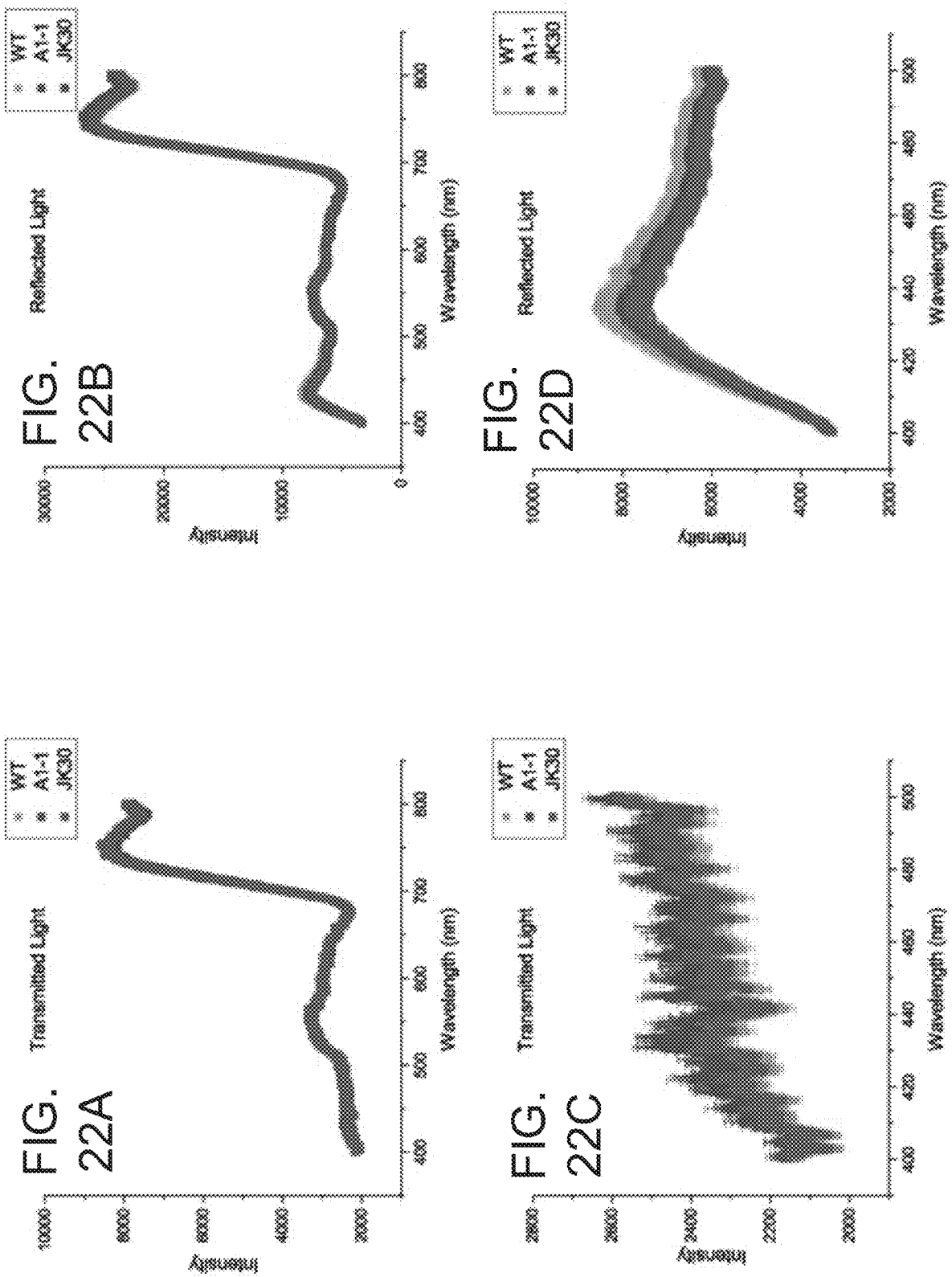

PLANTS HAVING INCREASED BIOMASS AND METHODS FOR MAKING THE SAME

CROSS REFERENCE TO RELATED APPLICATIONS

Benefit is claimed to the earlier filing date of U.S. Provisional Application No. 62/102,783, filed on Jan. 13, 2015, the disclosure of which is incorporated herein by reference in its entirety.

GOVERNMENT RIGHTS STATEMENT

This invention was made with government support under contract number DE-AR0000206 awarded by the United States Department of Energy. The government has certain rights in the invention.

FIELD

This document relates to methods and materials involved in modulating biomass levels in plants. For example, this document provides plants having increased biomass levels as well as materials and methods for making plants and plant products having increased biomass levels.

BACKGROUND

Plants having increased and/or improved biomass are useful for agriculture, horticulture, biomass to energy conversion, paper production, plant product production, and other industries. In particular, there is a need for increases in biomass for dedicated energy crops such as *Panicum virgatum* L. (switchgrass), *Miscanthus* x *gigantus* (*miscanthus*), *Sorghum* sp., and *Saccharum* sp. (sugar cane). Throughout human history, access to plant biomass for both food and fuel has been essential to maintaining and increasing population levels. Scientists are continually striving to improve biomass in agricultural crops. The large amount of research related to increasing plant biomass, particularly for dedicated energy crops, indicates the level of importance placed on providing sustainable sources of energy for the population. The urgency of developing sustainable and stable sources of plant biomass for energy is underscored by current events, such as rising oil prices. The amount of biomass produced by plants is a quantitative trait affected by a number of biochemical pathways.

SUMMARY

The instant disclosure relates to methods of producing a desired phenotype in a plant by manipulation of gene expression within the plant. The methods relate to decreasing the level of FtsZ gene expression or activity, wherein a desired phenotype, such as increased biomass relative to a wild-type control plant, is achieved. The instant disclosure also relates to nucleic acid sequences useful for such methods.

In embodiments, the present disclosure provides a method of producing a plant, the method comprising growing a plant cell comprising an exogenous nucleic acid, said exogenous nucleic acid comprising a regulatory region operably linked to a nucleotide sequence having at least 80% homology to SEQ ID NO: 1 or a portion or portions thereof wherein a plant produced from said plant cell has a difference in the level of biomass as compared to the corresponding level of a control plant that does not comprise said nucleic acid.

In embodiments, the present disclosure provides a method of regulating plant biomass levels, said method comprising introducing into a plant cell an exogenous nucleic acid, said exogenous nucleic acid comprising a nucleotide sequence having at least 80% homology to SEQ ID NO: 1 or a portion or portions thereof, and which does not comprise the exogenous nucleic acid as compared to the corresponding level in a control plant, from the plant cells to produce a differentiated plant biomass level.

In embodiments the present disclosure provides, a method for increasing the biomass of a plant, comprising modifying the expression of at least one plastid division protein in a plant. In embodiments the present disclosure provides, for increasing the biomass of a plant, comprising modifying the expression of at least one plastid division gene in a plant wherein modifying is decreasing and the plastid division gene can be FtsZ. In embodiments the plastid division protein can be FtsZ-1. In embodiments the present disclosure provides, a method of altering plant biomass comprising modifying expression of at least one FtsZ gene in a plant, wherein the biomass of the plant is increased when compared to a plant that lacks the reduced expression. In embodiments the present disclosure provides, a plant comprising decreased expression of at least one FtsZ gene, wherein the biomass of the plant is increased when compared to a plant that lacks the decreased expression. In certain embodiments the plant is a monocot. In other embodiments, the plant is a dicot.

More generally, there is provided herein a method for altering the biomass of a plant, comprising modifying the expression of at least one plastid division protein in a plant in order to increase plastid size and/or decrease plastid number, and plants produced by such methods. Optionally, such plants may also be modified to reduce the level of chlorophyll.

Also provided are plants and plant parts comprising an exogenous nucleic acid molecule the expression of which in the plant modifies expression of a plastid division gene compared to a wild-type control plant. Optionally, such plants and plant parts may also be modified to reduce the level of chlorophyll.

Another embodiment is a method of producing a plant having increased biomass accumulation relative to a wild-type plant, the method comprising introducing into a plant cell a nucleic acid construct that inhibits expression or activity of a plastid division gene, and regenerating a plant from that transformed plant cell, and plants produced by such methods. Optionally, such methods may include further introducing a nucleic acid that inhibits expression of a gene in order to reduce the level of chlorophyll.

Another provided embodiment is a method of producing a plant with increased biomass, comprising: modifying a plant cell to reduce expression of FtsZ1; producing from the plant cell a plant characterized by reduced expression of FtsZ1 compared to a control plant, wherein the plant has an increase in the level of biomass as compared to the corresponding level of the control plant. Optionally, such methods further comprise reducing the level of chlorophyll expression in the plant, for instance by inhibiting expression of magnesium chelatase and/or chlorophyll synthase.

Without wishing to be bound by any particular theory, there can be discussion herein of beliefs or understandings of underlying principles or mechanisms relating to embodiments of the disclosure. It is recognized that regardless of the ultimate correctness of any explanation or hypothesis, an embodiment of the disclosure can nonetheless be operative and useful.

The foregoing and other objects and features of the disclosure will become more apparent from the following detailed description, which proceeds with reference to the accompanying figures.

Further embodiments, forms, features, aspects, benefits, objects, and advantages of the present application shall become apparent from the detailed description and figures provided herewith.

DESCRIPTION OF THE DRAWINGS

This patent or application file contains at least one drawing executed in color. Copies of this patent or patent application publication with color drawings will be provided by the United States Patent and Trademark Office upon request and payment of the necessary fee.

FIG. 1A shows aboveground fresh weight in field grown sugarcane. Lines A1-1, JK-30 and B2-8 contain the FtsZ1 RNAi construct. Both A1-1 and JK-30 have increase in chloroplast volume. FIG. 1B. FtsZ1 Biomass as dry weight. Dry weight is a more reliable indicator of biomass than fresh weight.

FIG. 4A-4D show the sequence (SEQ ID NO: 1) and map of vector CSTiFtsz, which was used in the creation of sugarcane and *sorghum* RNAi lines. Also shown in FIG. 4A and FIG. 4B is the amino acid sequence of kanamycin (SEQ ID NO: 4; encoded at positions 1331 . . . 2122 of SEQ ID NO: 1).

FIG. 7A. Sugarcane with modified FtsZ expression during in the field during the 2014 field season. FIG. 7B. Transgene expression analysis of field grown FtsZ RNAi transgenic plants. Quantitative real-time RT-PCR analysis of FtsZ expression in WT (wild-type sugarcane) and FtsZ RNAi transgenic plants.

FIG. 12A. Percentage of blue light (460 nm) absorbed. FIG. 12B. Percentage of red light (635 nm) absorbed. FIG. 12C. Percentage of blue light (460 nm) reflected. FIG. 12D. Percentage of red light (635 nm) reflected.

FIG. 13A. Percentage of total light absorbed by *sorghum* leaves. FIG. 13B. Percentage of total light transmitted through *sorghum* leaves. FIG. 13C. Percentage of total light reflected by *sorghum* leaves. FIG. 13D. Profile of reflected light. FIG. 13E. Profile of transmitted light.

Figure 18A:
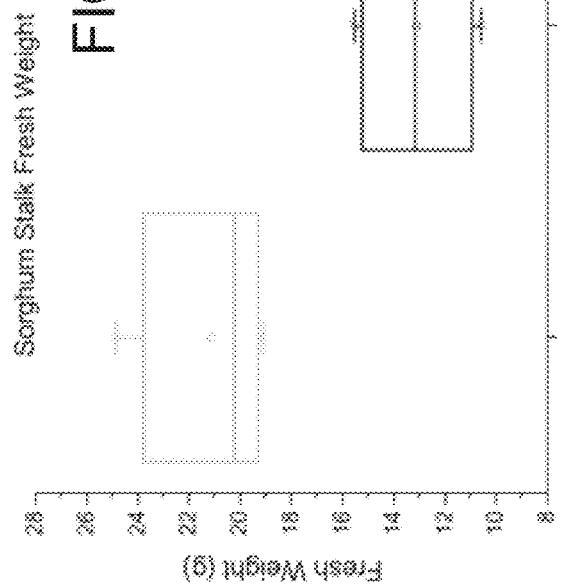
FIG. 18A-18D. Biomass production and related traits of FtsZ RNAi transgenic line 5A compared to non-transgenic wild-type *sorghum* plants under greenhouse conditions.
Figure 18C:
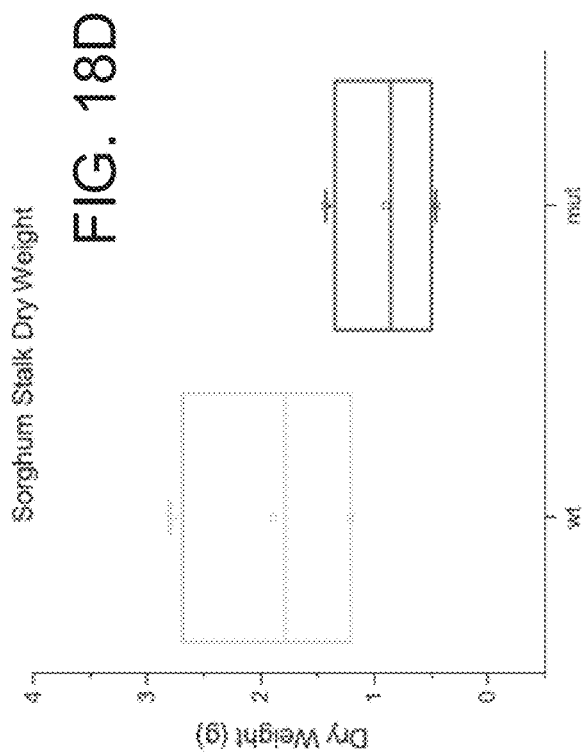
Figure 18B:
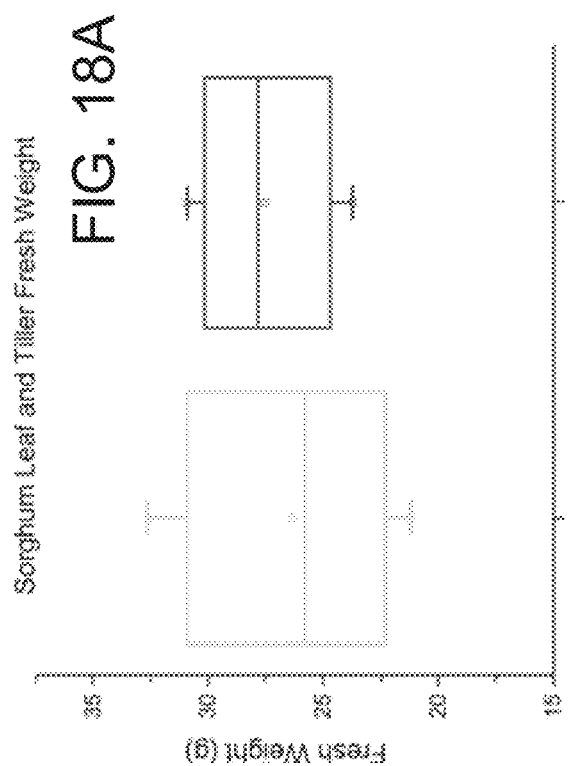
Figure 18D:
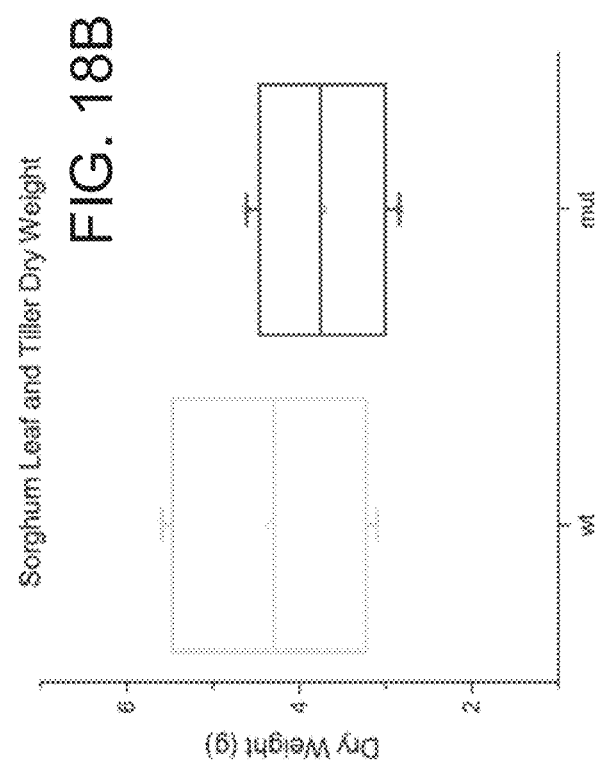

Fresh (FIG. 18A) and dry weights (FIG. 18B) of leaves and side tillers. Fresh (FIG. 18C) and dry (FIG. 18D) of main stalk.

FIG. 19. FtsZ1 expression in field grown sugarcane plants transformed with FtsZ1 RNAi. A 90% decrease in expression of FtsZ1 RNA was observed in both 2014 and 2015 field seasons confirming the knock-down of gene expression is stable. Green bar are the 2014 cane growth, yellow bars are the 2015 ratoon.

FIG. 20. Net assimilation rates of 2015 ratoon plants. During the second season of growth sugarcane plants with increased chloroplast size also had increased photosynthetic rates. The statistical means of both lines A1-1 and JK30 is higher than the wild type line. Statistical analysis was done by one-way ANOVA.

FIG. 21. End of season fresh aboveground biomass of FtsZ1 RNAi sugarcane lines. During both the 2014 season (green bars) and 2015 (yellow bars) lines with an increase in chloroplast size have greater end of season biomass.

FIG. 22A-22D. Measurements of transmitted and reflected light from field grown sugarcane with increased chloroplast size. Upper panels (FIGS. 22A & 22B) span wavelengths from 400 to 850 nm Lower panels (FIGS. 22C & 22D) are close-up of 400 to 500 nm (blue wavelength).

SEQUENCE LISTING

The nucleic and amino acid sequences listed in the accompanying sequence listing are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand. The Sequence Listing is submitted as an ASCII text file named 96178-02_SeqList-.txt, created on Apr. 26, 2016, ~16 KB, which is incorporated by reference herein.

SEQ ID NO: 1 is the nucleic acid sequence of vector CSTiFtsz, which was used in the creation of sugarcane and *sorghum* RNAi lines. Features in this vector include:
  FtsZ from *Saccharum officinarum*—Sense FtsZ exon (FtsZ 12 . . . 248) and antisense FtsZ exon (FtsZ 579 . . . 343)
  Intron (BG\Intron 249 . . . 342): 94 bp of 4-coumarate: CoA ligase (4CL) intron from bahia grass (*Paspalum notatum*), between sense and antisense exons of gene of interest (FtsZ)
  Terminator (CaMV\PolyA 598 . . . 810): T35S terminator from Cauliflower mosaic caulimovirus—T35S terminator is the poly A signal from CaMV; Feature 35SR3 647 . . . 626 is part of the terminator sequence
  Promoter (e35S 7412 . . . 8058): 35S CaMV promoter from Cauliflower mosaic caulimovirus, used to control expression of gene of interest
  kanamycin\(R) 1331 . . . 2122: bacterial selectable marker (SEQ ID NO: 4)
  pBR322\ori 2416 . . . 2696: bacterial origin of replication
  pBR322\bom 2836 . . . 3096: basis of mobility (bom), allows for conjugation
  pVS1\rep 3506 . . . 4506: bacterial origin of replication
  pVS1\sta 5099 . . . 6099: stability region
  pUC57F 7387 . . . 7404 & M13F 7387 . . . 7404: primer regions for sequencing SEQ ID NOs: 2 and 3 are representative forward (ScFtsZF) and reverse (ScFtsZR) primers used to amplify FtsZ.

DETAILED DESCRIPTION

The present disclosure relates to methods of modifying biomass in plants and plants generated thereby. In certain embodiments, modification of biomass may produce plants having increased biomass. In embodiments, the increased biomass may range from about 0.01% increase in biomass as compared to the wild type or control plant to greater than 100% increase in biomass as compared to the wild type or control plant.

FtsZ1 is a tubulin-like protein closely related to the bacterial protein FtsZ and has been shown to play a role in plastid division (Osteryoung & Vierling, Nature 376, 473-474, 1995; Strepp et al., Proc. Natl. Acad. Sci. USA 95, 4368-4373, 1998). FtsZ1 has been found in all plant species and thus is part of the so-called "greencut" proteins (Karpowicz et al. J. Biol. Chem. 286: 21427-21439, 2011)—nuclear encoded proteins that have resulted from gene transfer from progenitor endosymbiont. With its partner FtsZ2, FtsZ1 forms a contractile ring (the stromal Z ring) along the inner plastid membrane. In conjunction with a second ring outside the plastid, the plastid is pinched in half. Altering FtsZ1 expression has a negative impact on plastid division, which results in changes in plastid size. This change in size is dose dependent, where a small decrease in FtsZ1 expression results in a slight increase in plastid size while in plants with a larger decrease in expression there is a significant increase in plastid size. In some instances, one single large plastid is present in a cell.

Figure 1A:
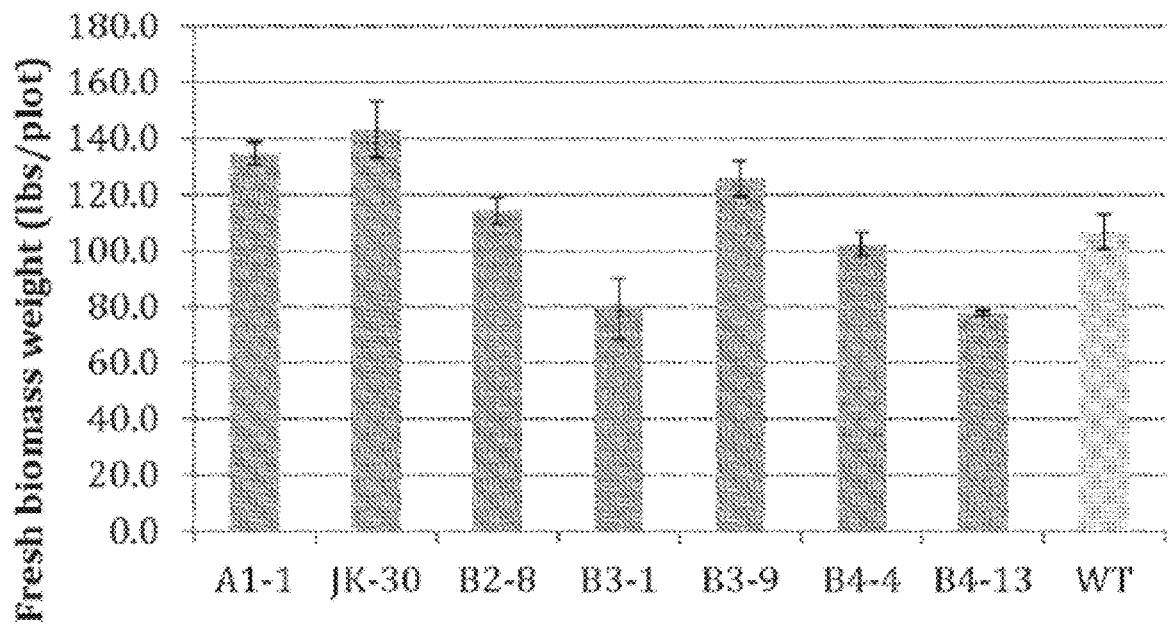
FIG. 1A-1B.
Figure 1B:
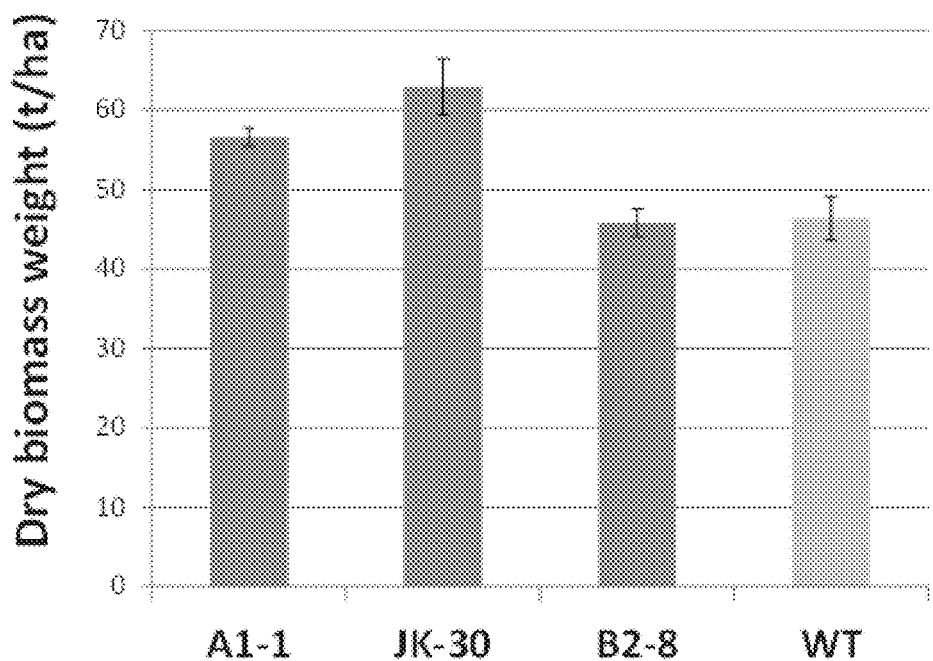
Figure 2:
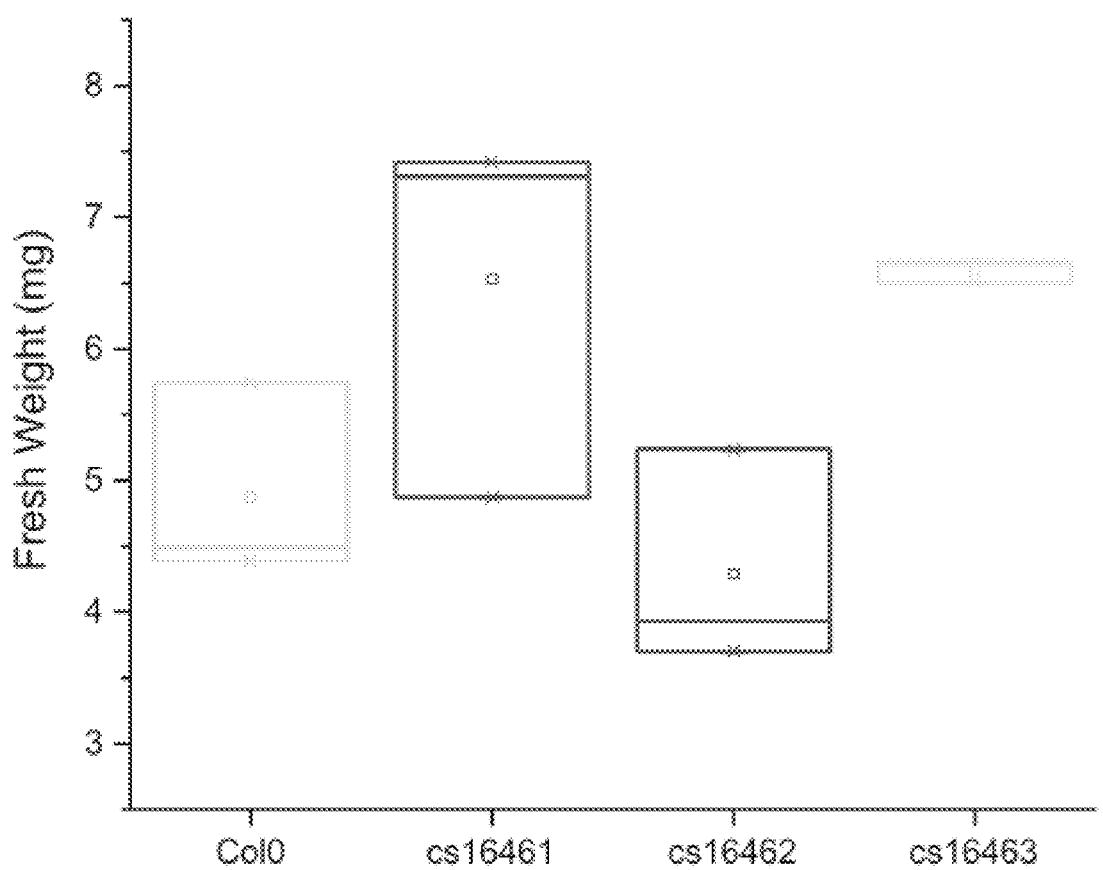
FIG. 2. Aboveground fresh weight biomass in *Arabidopsis thaliana*. The fresh weight was taken for three plants of each line at 11 weeks of growth. One-way ANOVA, standard error means was done. The three lines were selected from the publicly available database ABRC; cs16461 (atftsZ1-1 (G267R); giant chloroplasts), cs16462 (atftsZ1-1(delta404-433); slightly enlarged), and cs16463 (atftsZ1-1 (D159N); heterogeneous size population).

The impact of plastid size change in both the C4 monocot sugarcane (*Saccharine officinarum*) and C3 dicot *Arabidopsis* (*Arabidopsis thaliana*) has been examined. In both instances an impact in aboveground biomass was found; when plastid size is increased there is an increase in biomass relative to the parental lines (FIGS. 1A & 1B [sugarcane] and FIG. 2 [*Arabidopsis*]).

In the case of sugarcane, the plants were transformed with an FtsZ1 RNAi construct (FIG. 3) to decrease the expression of the protein and form transformed sugarcane lines.

*Sorghum* (*Sorghum bicolor*) has also been transformed with FtsZ1 RNAi construct (FIG. 3) construct and four independent lines with large chloroplasts have been generated and identified.

There is provided in a first embodiment a method for altering the biomass of a plant, the method involving modifying the expression of at least one plastid division protein (such as FtsZ1, FtsZ2, ARC6, PARC6, PDV1, PDV2, DRP5B (ARC5), PDR1, ARC3, MinD (ARC11), MinE (ARC12), MCD1, MinC-like, GC1, CLMP1, or CLR) in a plant in order to increase plastid size and/or decrease plastid number. In particular examples of such methods, modifying expression is decreasing expression, and the plastid division protein is FtsZ1, MinD, ARC6, PDV2, ARC3, MinE, or GC1.

Another embodiment is a method of increasing plant biomass comprising decreasing expression of at least one FtsZ gene in a plant, wherein the biomass of the plant is thereby increased compared to a plant in which the FtsZ gene expression is not modified. For instance, in examples of such methods the FtsZ gene is FtsZ-1 and modifying its expression comprises RNAi inhibition or CRISPR/Cas9 inhibition.

Also provided herein are plants (either monocot or dicot) and plant parts comprising an exogenous nucleic acid molecule the expression of which in the plant modifies expression of a plastid division gene compared to a wild-type control plant. By way of example, in some such plant and plant part the plastid division gene is selected from a gene encoding a protein selected from among FtsZ1, FtsZ2, ARC6, PARC6, PDV1, PDV2, DRP5B (ARC5), PDR1, ARC3, MinD (ARC11), MinE (ARC12), MCD1, MinC-like, GC1, CLMP1, and CLR.

In certain examples of the provided plants and plant parts, the exogenous nucleic acid molecule decreases expression of at least one FtsZ gene, and the biomass of the plant is thereby increased when compared to a plant that in which the FtsZ gene expression is not reduced. For instance, in some examples the at least one FtsZ gene is FtsZ-1.

Without limitation, the plants and plant parts may be of corn, *sorghum*, sugarcane, *Miscanthus*, switchgrass, *Setaria*, or cordgrass; or they may be of soybean, cotton, tobacco, pepper, potato, or tomato.

Also provided are seeds that produce any of the plants described herein, as well as seed produced by any of these plants.

Yet another embodiment provides a method of producing a plant having increased biomass accumulation relative to a wild-type plant, the method comprising introducing into a plant cell a nucleic acid construct that inhibits expression or activity of a plastid division gene, and regenerating a plant from that transformed plant cell. Plants produced by such methods are also contemplated herein.

In examples of methods of producing a plant having increased biomass accumulation, the method involves providing a nucleic acid vector comprising a promoter operably linked to a nucleic acid construct that modifies plastid division gene expression or activity; transforming a plant, tissue culture, or a plant cell with the vector to obtain a plant, tissue culture or a plant cell with modified plastid division gene expression or activity; and growing the plant or regenerating a plant from the tissue culture or plant cell, thereby producing a plant having increased biomass accumulation relative to a wild-type plant.

Another embodiment is a method of producing a plant with increased biomass, the method involving modifying a plant cell to reduce expression of FtsZ1; producing from the plant cell a plant characterized by reduced expression of FtsZ1 compared to a control plant, wherein the plant has an increase in the level of biomass as compared to the corresponding level of the control plant.

Optionally, the methods herein further involve reducing the level of chlorophyll expression in the plant, for instance by inhibiting expression of magnesium chelatase and/or chlorophyll synthase. Thus, plants having both enlarged chloroplasts (and/or decreased chloroplast number) and reduced chlorophyll are contemplated.

Definitions of Terms

Unless otherwise explained, all technical and scientific terms used herein have the same meaning as commonly understood by one of ordinary skill in the art to which a disclosed disclosure belongs. The singular terms "a," "an," and "the" include plural referents unless context clearly indicates otherwise. Similarly, the word "or" is intended to include "and" unless the context clearly indicates otherwise.

As used herein, "comprising" is synonymous with "including," "containing," or "characterized by," and is inclusive or open-ended and does not exclude additional, un-recited elements or method steps. "Comprising A or B" means "including A" or "including B" or "including A and B." As used herein, "consisting of" excludes any element, step, or ingredient not specified in the aspect element. As used herein, "consisting essentially of" does not exclude materials or steps that do not materially affect the basic and novel characteristics of the aspect. In each instance herein any of the terms "comprising", "consisting essentially of" and "consisting of" may be replaced with either of the other two terms. The disclosure illustratively described herein suitably may be practiced in the absence of any element or elements, limitation or limitations which is not specifically disclosed herein.

While the present disclosure can take many different forms, for the purpose of promoting an understanding of the principles of the disclosure, reference will now be made to the embodiments illustrated in the drawings and specific language will be used to describe the same. It will nevertheless be understood that no limitation of the scope of the disclosure is thereby intended. Any alterations and further modifications of the described embodiments, and any further applications of the principles of the disclosure as described herein are contemplated as would normally occur to one skilled in the art to which the disclosure relates.

The terms and expressions which have been employed herein are used as terms of description and not of limitation, and there is no intention in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments, exemplary embodiments and optional features, modification and variation of the concepts herein disclosed may be resorted to by those skilled in the art, and that such modifications and variations are considered to be within the scope of this disclosure as defined by the appended aspects. The specific embodiments provided herein are examples of useful embodiments of the present disclosure and it will be apparent to one skilled in the art that the present disclosure may be carried out using a large number of variations of the devices, device components, methods steps set forth in the present description. As will be obvious to one of skill in the art, methods and devices useful for the present methods can include a large number of optional composition and processing elements and steps.

"Allele" means any of one or more alternative forms of a genetic sequence. In a diploid cell or organism, the two alleles of a given sequence typically occupy corresponding loci on a pair of homologous chromosomes. With regard to a SNP marker, allele refers to the specific nucleotide base present at that SNP locus in that individual plant.

The term "amplifying" in the context of nucleic acid amplification is any process whereby additional copies of a selected nucleic acid (or a transcribed form thereof) are produced. An "amplicon" is an amplified nucleic acid, e.g., a nucleic acid that is produced by amplifying a template nucleic acid by any available amplification method.

"Backcrossing" is a process in which a breeder crosses a progeny variety back to one of the parental genotypes one or more times.

The term "chromosome segment" designates a contiguous linear span of genomic DNA that resides in planta on a single chromosome. "Chromosome interval" refers to a chromosome segment defined by specific flanking marker loci.

A coding sequence is the part of a gene or cDNA which codes for the amino acid sequence of a protein, or for a functional RNA such as a tRNA or rRNA.

Complement or complementary sequence means a sequence of nucleotides which forms a hydrogen-bonded duplex with another sequence of nucleotides according to Watson-Crick base-pairing rules.

"Cultivar" and "variety" are used synonymously and mean a group of plants within a species (e.g., *Glycine max*) that share certain genetic traits that separate them from other possible varieties within that species. Soybean cultivars are inbred lines produced after several generations of self-pollinations. Individuals within a soybean cultivar are homogeneous, nearly genetically identical, with most loci in the homozygous state.

Downstream refers to a relative position in DNA or RNA and is the region towards the 3' end of a strand.

An "elite line" is an agronomically superior line that has resulted from many cycles of breeding and selection for superior agronomic performance. Numerous elite lines are available and known to those of skill in the art of soybean breeding.

An "elite population" is an assortment of elite individuals or lines that can be used to represent the state of the art in terms of agronomically superior genotypes of a given crop species, such as soybean.

An "exotic soybean strain" or an "exotic soybean germplasm" is a strain or germplasm derived from a soybean not belonging to an available elite soybean line or strain of germplasm. In the context of a cross between two soybean plants or strains of germplasm, an exotic germplasm is not closely related by descent to the elite germplasm with which it is crossed. Most commonly, the exotic germplasm is not derived from any known elite line of soybean, but rather is selected to introduce novel genetic elements (typically novel alleles) into a breeding program.

Expression refers to the transcription of a gene into structural RNA (rRNA, tRNA) or messenger RNA (mRNA) and subsequent translation of an mRNA into a protein.

A "genetic map" is a description of genetic linkage relationships among loci on one or more chromosomes (or linkage groups) within a given species, generally depicted in a diagrammatic or tabular form.

"Genotype" refers to the genetic constitution of a cell or organism.

"Germplasm" refers to the genetic material that comprises the physical foundation of the hereditary qualities of an organism. As used herein, germplasm includes seeds and living tissue from which new plants may be grown; or, another plant part, such as leaf, stem, pollen, or cells, that may be cultured into a whole plant. Germplasm resources provide sources of genetic traits used by plant breeders to improve commercial cultivars.

"Grain" is intended to mean the mature seed produced by commercial growers for purposes other than growing or reproducing the species.

An individual is "homozygous" if the individual has only one type of allele at a given locus (e.g., a diploid individual has a copy of the same allele at a locus for each of two homologous chromosomes). An individual is "heterozygous" if more than one allele type is present at a given locus (e.g., a diploid individual with one copy each of two different alleles). The term "homogeneity" indicates that members of a group have the same genotype at one or more specific loci. In contrast, the term "heterogeneity" is used to indicate that individuals within the group differ in genotype at one or more specific loci.

"Haplotype" refers to a combination of particular alleles present within a particular plant's genome at two or more linked marker loci, for instance at two or more loci on a particular linkage group. For instance, in one example, two specific marker loci on LG-O are used to define a haplotype for a particular plant. In still further examples, 3, 4, 5, 6, 7, 8, 9, 10, 11, 12, 13, 14, 15, 16, 17, 18, 19, 20, or more linked marker loci are used to define a haplotype for a particular plant.

Two nucleic acid sequences are "heterologous" to one another if the sequences are derived from separate organisms, whether or not such organisms are of different species, as long as the sequences do not naturally occur together in the same arrangement in the same organism.

"Homology" refers to the extent of identity between two nucleotide or amino acid sequences.

"Introgression" refers to the entry or introduction of a gene, QTL, marker, haplotype, marker profile, trait, or trait locus from the genome of one plant into the genome of another plant.

Isolated refers to being altered by the hand of man from the natural state. If an "isolated" composition or substance occurs in nature, it has been changed or removed from its original environment, or both. For example, a polynucleotide or a polypeptide naturally present in a living animal is not isolated, but the same polynucleotide or polypeptide separated from the coexisting materials of its natural state is isolated, as the term is employed herein.

A nucleic acid construct is a nucleic acid molecule which is isolated from a naturally occurring gene or which has been modified to contain segments of nucleic acid which are combined and juxtaposed in a manner which would not otherwise exist in nature.

The terms "label" and "detectable label" refer to a molecule capable of detection. A detectable label can also include a combination of a reporter and a quencher, such as are employed in FRET probes or TaqMan™ probes. The term "reporter" refers to a substance or a portion thereof which is capable of exhibiting a detectable signal, which signal can be suppressed by a quencher. The detectable signal of the reporter is, e.g., fluorescence in the detectable range. The term "quencher" refers to a substance or portion thereof which is capable of suppressing, reducing, inhibiting, etc., the detectable signal produced by the reporter. As used herein, the terms "quenching" and "fluorescence energy transfer" refer to the process whereby, when a reporter and a quencher are in close proximity, and the reporter is excited by an energy source, a substantial portion of the energy of the excited state non-radiatively transfers to the quencher where it either dissipates non-radiatively or is emitted at a different emission wavelength than that of the reporter.

A "line" or "strain" is a group of individuals of identical parentage that are generally inbred to some degree and that are generally homozygous and homogeneous at most loci (isogenic or near isogenic). A "subline" refers to an inbred subset of descendants that are genetically distinct from other similarly inbred subsets descended from the same progenitor. Traditionally, a subline has been derived by inbreeding the seed from an individual soybean plant selected at the F3 to F5 generation until the residual segregating loci are "fixed" or homozygous across most or all loci. Commercial soybean varieties (or lines) are typically produced by aggregating ("bulking") the self-pollinated progeny of a single F3 to F5 plant from a controlled cross between 2 genetically different parents. While the variety typically appears uniform, the self-pollinating variety derived from the selected plant eventually (e.g., F8) becomes a mixture of homozygous plants that can vary in genotype at any locus that was heterozygous in the originally selected F3 to F5 plant. Marker-based sublines that differ from each other based on qualitative polymorphism at the DNA level at one or more specific marker loci are derived by genotyping a sample of seed derived from individual self-pollinated progeny derived from a selected F3-F5 plant. The seed sample can be genotyped directly as seed, or as plant tissue grown from such a seed sample. Optionally, seed sharing a common genotype at the specified locus (or loci) are bulked providing a subline that is genetically homogenous at identified loci important for a trait of interest (e.g., yield, tolerance, etc.).

"Linkage" refers to a phenomenon wherein alleles on the same chromosome tend to segregate together more often than expected by chance if their transmission was independent. Genetic recombination occurs with an assumed random frequency over the entire genome. Genetic maps are constructed by measuring the frequency of recombination between pairs of traits or markers. The closer the traits or markers are to each other on the chromosome, the lower the frequency of recombination, and the greater the degree of linkage. Traits or markers are considered herein to be linked if they generally co-segregate. A 1/100 probability of recombination per generation is defined as a map distance of 1.0 centiMorgan (1.0 cM). The genetic elements or genes located on a single chromosome segment are physically linked. Two loci can be located in close proximity such that recombination between homologous chromosome pairs does not occur between the two loci during meiosis with high frequency, e.g., such that linked loci co-segregate at least about 90% of the time, e.g., 91%, 92%, 93%, 94%, 95%, 96%, 97%, 98%, 99%, 99.5%, 99.75%, or more of the time. The genetic elements located within a chromosome segment are also genetically linked, typically within a genetic recombination distance of less than or equal to 50 centimorgans (cM), e.g., about 49, 40, 30, 20, 10, 9, 8, 7, 6, 5, 4, 3, 2, 1, 0.75, 0.5, or 0.25 cM or less. That is, two genetic elements within a single chromosome segment undergo recombination during meiosis with each other at a frequency of less than or equal to about 50%, e.g., about 49%, 40%, 30%, 20%, 10%, 9%, 8%, 7%, 6%, 5%, 4%, 3%, 2%, 1%, 0.75%, 0.5%, or 0.25% or less. Closely linked markers display a cross over frequency with a given marker of about 10% or less (the given marker is within about 10 cM of a closely linked marker). Put another way, closely linked loci co-segregate at least about 90% of the time. With regard to physical position on a chromosome, closely linked markers can be separated, for example, by about 1 megabase (Mb; 1 million nucleotides), about 500 kilobases (Kb; 1000 nucleotides), about 400 Kb, about 300 Kb, about 200 Kb, about 100 Kb, about 50 Kb, about 25 Kb, about 10 Kb, about 5 Kb, about 4 Kb, about 3 Kb, about 2 Kb, about 1 Kb, about 500 nucleotides, about 250 nucleotides, or less.

When referring to the relationship between two genetic elements, such as a genetic element contributing to tolerance and a proximal marker, "coupling" phase linkage indicates the state where the "favorable" allele at the tolerance locus is physically associated on the same chromosome strand as the "favorable" allele of the respective linked marker locus. In coupling phase, both favorable alleles are inherited together by progeny that inherit that chromosome strand. In "repulsion" phase linkage, the "favorable" allele at the locus of interest (e.g., a QTL for tolerance) is physically linked with an "unfavorable" allele at the proximal marker locus, and the two "favorable" alleles are not inherited together (i.e., the two loci are "out of phase" with each other).

"Linkage disequilibrium" refers to a phenomenon wherein alleles tend to remain together in linkage groups when segregating from parents to offspring, with a greater frequency than expected from their individual frequencies.

"Linkage group" refers to traits or markers that generally co-segregate. A linkage group generally corresponds to a chromosomal region containing genetic material that encodes the traits or markers.

"Locus" is a defined segment of DNA.

A "map location" or "map position" or "relative map position" is an assigned location on a genetic map relative to linked genetic markers where a specified marker can be found within a given species. Map positions are generally provided in centimorgans. A "physical position" or "physical location" or "physical map location" is the position, typically in nucleotide bases, of a particular nucleotide, such as a SNP nucleotide, on a chromosome.

"Mapping" is the process of defining the linkage relationships of loci through the use of genetic markers, populations segregating for the markers, and standard genetic principles of recombination frequency.

"Marker" or "molecular marker" is a term used to denote a nucleic acid or amino acid sequence that is sufficiently unique to characterize a specific locus on the genome. Any detectable polymorphic trait can be used as a marker so long as it is inherited differentially and exhibits linkage disequilibrium with a phenotypic trait of interest. A number of soybean markers have been mapped and linkage groups created, as described in Cregan et al., "An Integrated Genetic Linkage Map of the Soybean Genome" (1999) Crop Science 39:1464-90, and more recently in Choi, et al., "A Soybean Transcript Map: Gene Distribution, Haplotype and Single-Nucleotide Polymorphism Analysis" (2007) Genetics 176:685-96. Many soybean markers are publicly available at the USDA affiliated soybase website (soybase.org). All markers are used to define a specific locus on the soybean genome. Large numbers of these markers have been mapped. Each marker is therefore an indicator of a specific segment of DNA, having a unique nucleotide sequence. The map positions provide a measure of the relative positions of particular markers with respect to one another. When a trait is stated to be linked to a given marker it will be understood that the actual DNA segment whose sequence affects the trait generally co-segregates with the marker. More precise and definite localization of a trait can be obtained if markers are identified on both sides of the trait. By measuring the appearance of the marker(s) in progeny of crosses, the existence of the trait can be detected by relatively simple molecular tests without actually evaluating the appearance of the trait itself, which can be difficult and time-consuming because the actual evaluation of the trait requires growing plants to a stage and/or under environmental conditions where the trait can be expressed. Molecular markers have been widely used to determine genetic composition in soybeans. "Marker assisted selection" refers to the process of selecting a desired trait or traits in a plant or plants by detecting one or more nucleic acids from the plant, where the nucleic acid is linked to the desired trait, and then selecting the plant or germplasm possessing those one or more nucleic acids.

"Nucleic acid molecule" refers to a single- or double-stranded linear polynucleotide containing either deoxyribonucleotides or ribonucleotides that are linked by 3'-5'-phosphodiester bonds.

Two DNA sequences are "operably linked" if the nature of the linkage does not interfere with the ability of the sequences to affect their normal functions relative to each other. For instance, a promoter region would be operably linked to a coding sequence if the promoter were capable of effecting transcription of that coding sequence.

The term "plant" includes reference to an immature or mature whole plant, including a plant from which seed or grain or anthers have been removed. Seed or embryo that will produce the plant is also considered to be the plant.

Any commercially or scientifically valuable plant is envisaged in accordance with these embodiments of the invention. Plants that are particularly useful in the methods of the invention include all plants which belong to the super family Viridiplantae, in particular monocotyledonous and dicotyledonous plants including a fodder or forage legume, ornamental plant, food crop, tree, or shrub selected from the list comprising *Acacia* spp., *Acer* spp., *Actinidia* spp., *Aesculus* spp., *Agathis australis*, *Albizia amara*, *Alsophila tricolor*, *Andropogon* spp., *Arachis* spp, *Areca catechu*, *Astelia fragrans*, *Astragalus cicer*, *Baikiaea plurijuga*, *Betula* spp., *Brassica* spp., *Bruguiera gymnorrhiza*, *Burkea africana*, *Butea frondosa*, *Cadaba farinosa*, *Calliandra* spp, *Camellia sinensis*, *Canna indica*, *Capsicum* spp., *Cassia* spp., *Centroema pubescens*, *Chacoomeles* spp., *Cinnamomum cassia*, *Coffea arabica*, *Colophospermum mopane*, *Coronillia varia*, *Cotoneaster serotina*, *Crataegus* spp., *Cucumis* spp., *Cupressus* spp., *Cyathea dealbata*, *Cydonia oblonga*, *Cryptomeria japonica*, *Cymbopogon* spp., *Cynthea dealbata*, *Cydonia oblonga*, *Dalbergia monetaria*, *Davallia divaricata*, *Desmodium* spp., *Dicksonia squarosa*, *Dibeteropogon amplectens*, *Dioclea* spp, *Dolichos* spp., *Dorycnium rectum*, *Echinochloa pyramidalis*, *Ehraffia* spp., *Eleusine coracana*, *Eragrestis* spp., *Erythrina* spp., *Eucalyptus* spp., *Euclea schimperi*, *Eulalia vi/losa*, *Pagopyrum* spp., *Feijoa sellowlana*, *Fragaria* spp., *Flemingia* spp, *Freycinetia banksli*, *Geranium thunbergii*, *GinAgo biloba*, *Glycine javanica*, *Gliricidia* spp, *Gossypium hirsutum*, *Grevillea* spp., *Guibourtia coleosperma*, *Hedysarum* spp., *Hemaffhia altissima*, *Heteropogon contoffus*, *Hordeum vulgare*, *Hyparrhenia rufa*, *Hypericum erectum*, *Hypeffhelia dissolute*, *Indigo incamata*, *Iris* spp., *Leptarrhena pyrolifolia*, *Lespediza* spp., *Lettuca* spp., *Leucaena leucocephala*, *Loudetia simplex*, *Lo tonus bainesli*, *Lotus* spp., *Macro tyloma axillare*, *Malus* spp., *Manihot esculenta*, *Medicago saliva*, *Metasequoia glyptostroboides*, *Musa sapientum*, *Nicotianum* spp., *Onobrychis* spp., *Ornithopus* spp., *Oryza* spp., *Peltophorum africanum*, *Pennisetum* spp., *Persea gratissima*, *Petunia* spp., *Phaseolus* spp., *Phoenix canadensis*, *Phormium cookianum*, *Photinia* spp., *Picea glauca*, *Pinus* spp., *Pisum sativam*, *Podocarpus totara*, *Pogonarthria fleckii*, *Pogonaffhria squarrosa*, *Populus* spp., *Prosopis cineraria*, *Pseudotsuga menziesii*, *Pterolobium stellatum*, *Pyrus communis*, *Quercus* spp., *Rhaphiolepsis umbellata*, *Rhopalostylis sapida*, *Rhus natalensis*, *Ribes grossularia*, *Ribes* spp., *Robinia pseudoacacia*, *Rosa* spp., *Rubus* spp., *Salix* spp., *Schyzachyrium sanguineum*, *Sciadopitys vefficillata*, *Sequoia sempervirens*, *Sequoiadendron giganteum*, *Sorghum bicolor*, *Spinacia* spp., *Sporobolus fimbriatus*, *Stiburus alopecuroides*, *Stylosanthos humilis*, *Tadehagi* spp, *Taxodium distichum*, *Themeda triandra*, *Trifolium* spp., *Triticum* spp., *Tsuga heterophylla*, *Vaccinium* spp., *Vicia* spp., *Vitis vinifera*, *Watsonia pyramidata*, *Zantedeschia aethiopica*, *Zea mays*, amaranth, artichoke, asparagus, broccoli, Brussels sprouts, cabbage, canola, carrot, cauliflower, celery, collard greens, flax, kale, lentil, oilseed rape, okra, onion, potato, rice, soybean, straw, sugar beet, sugar cane, sunflower, tomato, squash tea, maize, wheat, barley, rye, oat, peanut, pea, lentil and alfalfa, cotton, rapeseed, canola, pepper, sunflower, tobacco, eggplant, switchgrass, *Miscanthus*, *Setaria*, fescue, *eucalyptus*, a tree, an ornamental plant, a perennial grass and a forage crop. Alternatively algae and other non-Viridiplantae can be used for the methods of the present invention.

"Plant parts" means any portion or piece of a plant, including anthers, buds, cells (including cells in tissue culture), cotyledons, embryo, flowers, grain, hypocotyls, leaves, meristem, nodes, ovules, petioles, pistils, pods, pollen, protoplast, roots, root tips, seed, shoots, stalks, stems, tissues, tissue cultures, and so forth.

"Polymorphism" means a change or difference between two related nucleic acids. A "nucleotide polymorphism" refers to a nucleotide that is different in one sequence when compared to a related sequence when the two nucleic acids are aligned for maximal correspondence.

"Polynucleotide," "polynucleotide sequence," "nucleic acid sequence," "nucleic acid fragment," and "oligonucleotide" are used interchangeably herein. These terms encompass nucleotide sequences and the like. A polynucleotide is a polymer of nucleotides that is single- or multi-stranded, that optionally contains synthetic, non-natural, or altered RNA or DNA nucleotide bases. A DNA polynucleotide may be comprised of one or more strands of cDNA, genomic DNA, synthetic DNA, or mixtures thereof.

A polypeptide is a linear polymer of amino acids that are linked by peptide bonds.

"Primer" refers to an oligonucleotide (synthetic or occurring naturally), which is capable of acting as a point of initiation of nucleic acid synthesis or replication along a complementary strand when placed under conditions in which synthesis of a complementary strand is catalyzed by a polymerase. Typically, primers are about 10 to 30 nucleotides in length, but longer or shorter sequences can be employed. Primers may be provided in double-stranded form, though the single-stranded form is more typically used. A primer can further contain a detectable label, for example a 5' end label.

"Probe" refers to an oligonucleotide (synthetic or occurring naturally) that is complementary (though not necessarily fully complementary) to a polynucleotide of interest and forms a duplexed structure by hybridization with at least one strand of the polynucleotide of interest. Typically, probes are oligonucleotides from 10 to 50 nucleotides in length, but longer or shorter sequences can be employed. A probe can further contain a detectable label.

Promoter means a cis-acting DNA sequence, generally 80-120 base pairs long and located upstream of the initiation site of a gene, to which RNA polymerase may bind and initiate correct transcription. There can be associated additional transcription regulatory sequences which provide on/off regulation of transcription and/or which enhance (increase) expression of the downstream coding sequence.

"Quantitative trait loci" or "QTL" refer to the genetic elements controlling a quantitative trait.

A recombinant nucleic acid molecule, for instance a recombinant DNA molecule, is a novel nucleic acid sequence formed in vitro through the ligation of two or more non-homologous DNA molecules (for example a recombinant plasmid containing one or more inserts of foreign DNA cloned into at least one cloning site).

"Recombination frequency" is the frequency of a crossing over event (recombination) between two genetic loci. Recombination frequency can be observed by following the segregation of markers and/or traits during meiosis.

"Self-crossing" or "self-pollination" or "selfing" is a process through which a breeder crosses a plant with itself; for example, a second generation hybrid F2 with itself to yield progeny designated F2:3.

"SNP" or "single nucleotide polymorphism" means a sequence variation that occurs when a single nucleotide (A, T, C, or G) in the genome sequence is altered or variable. "SNP markers" exist when SNPs are mapped to sites on the soybean genome.

Transformation refers to the directed modification of the genome of a cell by the external application of purified recombinant DNA from another cell of different genotype, leading to its uptake and integration into the subject cell's genome. In bacteria, the recombinant DNA is not typically integrated into the bacterial chromosome, but instead replicates autonomously as a plasmid.

Upstream means on the 5' side of any site in DNA or RNA.

A vector is a nucleic acid molecule that is able to replicate autonomously in a host cell and can accept foreign DNA. A vector carries its own origin of replication, one or more unique recognition sites for restriction endonucleases which can be used for the insertion of foreign DNA, and usually selectable markers such as genes coding for antibiotic resistance, and often recognition sequences (e.g. promoter) for the expression of the inserted DNA. Common vectors include plasmid vectors and phage vectors.

The term "yield" refers to the productivity per unit area of a particular plant product of commercial value. For example, yield of soybean is commonly measured in bushels of seed per acre or metric tons of seed per hectare per season. Yield is affected by both genetic and environmental factors. Yield is the final culmination of all agronomic traits.

A "subject plant or plant cell" is one in which genetic alteration, such as transformation, has been affected as to a gene of interest, or is a plant or plant cell which is descended from a plant or cell so altered and which comprises the alteration. A "control" or "control plant" or "control plant cell" provides a reference point for measuring changes in phenotype of the subject plant or plant cell.

A control plant or plant cell may comprise, for example: (a) a wild-type plant or cell, i.e., of the same genotype as the starting material for the genetic alteration which resulted in the subject plant or cell; (b) a plant or plant cell of the same genotype as the starting material but which has been transformed with a null construct (i.e. with a construct which has no known effect on the trait of interest, such as a construct comprising a marker gene); (c) a plant or plant cell which is a non-transformed segregant among progeny of a subject plant or plant cell; (d) a plant or plant cell genetically identical to the subject plant or plant cell but which is not exposed to conditions or stimuli that would induce expression of the gene of interest; or (e) the subject plant or plant cell itself, under conditions in which the gene of interest is not expressed.

As used herein, an "isolated" or "purified" polynucleotide or polypeptide, or biologically active portion thereof, is substantially or essentially free from components that normally accompany or interact with the polynucleotide or polypeptide as found in its naturally occurring environment. Thus, an isolated or purified polynucleotide or polypeptide is substantially free of other cellular material or culture medium when produced by recombinant techniques, or substantially free of chemical precursors or other chemicals when chemically synthesized. Optimally, an "isolated" polynucleotide is free of sequences (optimally protein encoding sequences) that naturally flank the polynucleotide (i.e., sequences located at the 5' and 3' ends of the polynucleotide) in the genomic DNA of the organism from which the polynucleotide is derived. For example, in various embodiments, the isolated polynucleotide can contain less than about 5 kb, 4 kb, 3 kb, 2 kb, 1 kb, 0.5 kb, or 0.1 kb of nucleotide sequence that naturally flank the polynucleotide in genomic DNA of the cell from which the polynucleotide is derived. A polypeptide that is substantially free of cellular material includes preparations of polypeptides having less than about 30%, 20%, 10%, 5%, or 1% (by dry weight) of contaminating protein. When the polypeptide of the invention or biologically active portion thereof is recombinantly produced, optimally culture medium represents less than about 30%, 20%, 10%, 5%, or 1% (by dry weight) of chemical precursors or non-protein-of-interest chemicals.

Standard recombinant DNA and molecular cloning techniques used herein are well known in the art and are described more fully in Sambrook, J., Fritsch, E. F. and Maniatis, T. Molecular Cloning: A Laboratory Manual; Cold Spring Harbor Laboratory Press Cold Spring Harbor, 1989 (hereinafter "Sambrook").

"Tolerance and "improved tolerance" are used interchangeably herein and refer to any type of increase in resistance or tolerance to, or any type of decrease in susceptibility. A "tolerant plant" or "tolerant plant variety" need not possess absolute or complete tolerance. Instead, a "tolerant plant," "tolerant plant variety," or a plant or plant variety with "improved tolerance" will have a level of resistance or tolerance which is higher than that of a comparable susceptible plant or variety.

Whenever a range is given in the specification, for example, a temperature range, a time range, or a composition or concentration range, all intermediate ranges and subranges, as well as all individual values included in the ranges given are intended to be included in the disclosure. It will be understood that any subranges or individual values in a range or subrange that are included in the description herein can be excluded from the aspects herein.

All patents and publications mentioned in the specification are indicative of the levels of skill of those skilled in the art to which the disclosure pertains. References cited herein are incorporated by reference herein in their entirety to indicate the state of the art as of their publication or filing date and it is intended that this information can be employed herein, if needed, to exclude specific embodiments that are in the prior art. For example, when compositions of matter are disclosed, it should be understood that compounds known and available in the art prior to Applicant's disclosure, including compounds for which an enabling disclosure is provided in the references cited herein, are not intended to be included in the composition of matter aspects herein. A reference that is partially inconsistent with the disclosure herein is incorporated by reference except for the partially inconsistent portion of the reference One of ordinary skill in the art will appreciate that starting materials, biological materials, reagents, synthetic methods, purification methods, analytical methods, assay methods, and biological methods other than those specifically exemplified can be employed in the practice of the disclosure without resort to undue experimentation. All art-known functional equivalents, of any such materials and methods are intended to be included in this disclosure. The terms and expressions which have been employed are used as terms of description and not of limitation, and there is no intention that in the use of such terms and expressions of excluding any equivalents of the features shown and described or portions thereof, but it is recognized that various modifications are possible within the scope of the disclosure. Thus, it should be understood that although the present disclosure has been specifically disclosed by preferred embodiments and optional features, modification and variation of the concepts herein disclosed may be resorted to by those skilled in the art, and that such modifications and variations are considered to be within the scope of this disclosure as defined by the appended aspects.

Although the present disclosure has been described with reference to certain embodiments thereof, other embodiments are possible without departing from the present disclosure. The spirit and scope of the appended aspects should not be limited, therefore, to the description of the preferred embodiments contained herein. All embodiments that come within the meaning of the aspects, either literally or by equivalence, are intended to be embraced therein. Furthermore, the advantages described above are not necessarily the only advantages of the disclosure, and it is not necessarily expected that all of the described advantages will be achieved with every embodiment of the disclosure.

Methods of Increasing Biomass in Plants

Figure 3:
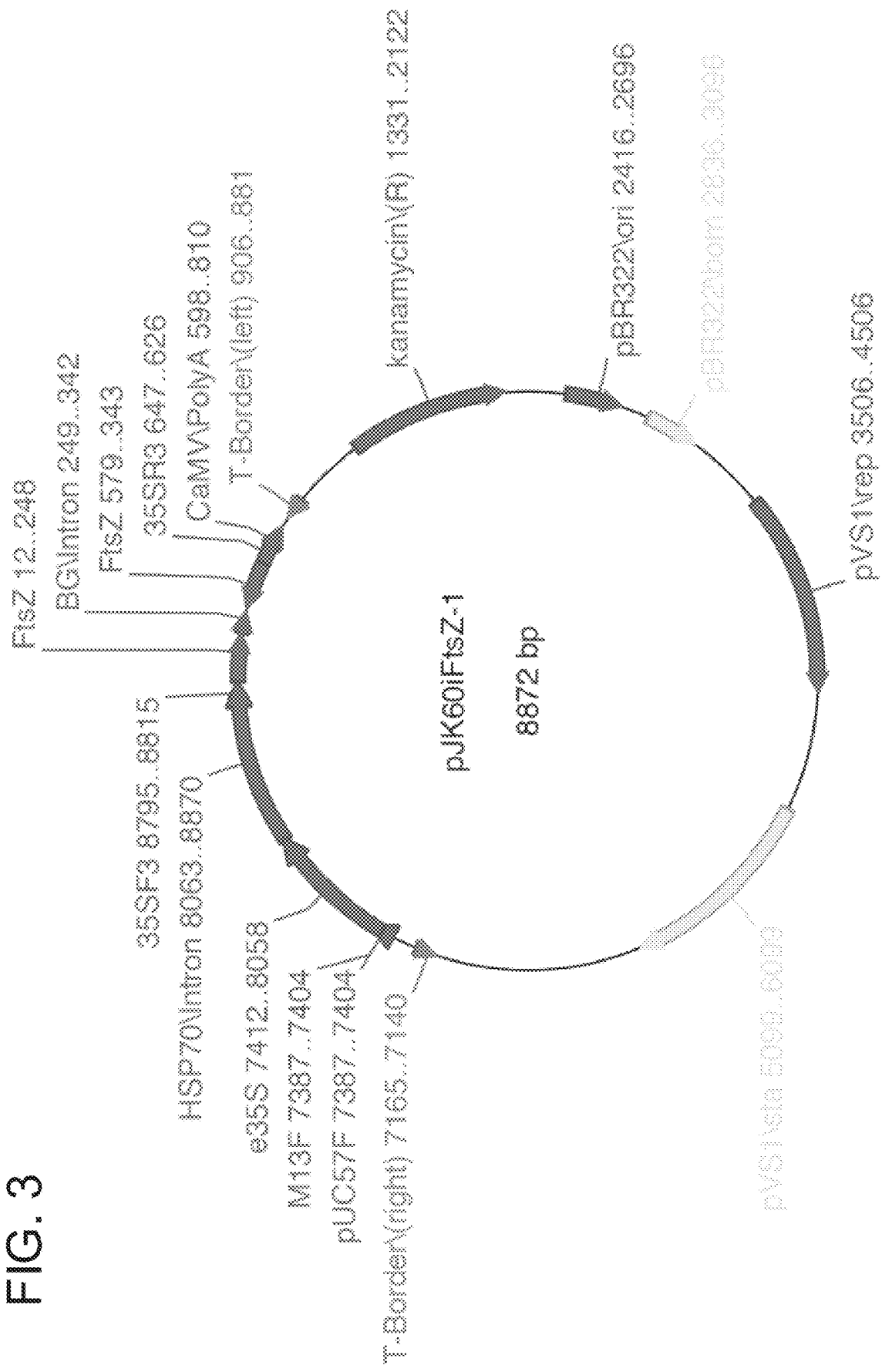
FIG. 3. Plasmid map used in the creation of sugarcane and *sorghum* RNAi lines.
Figure 4A:
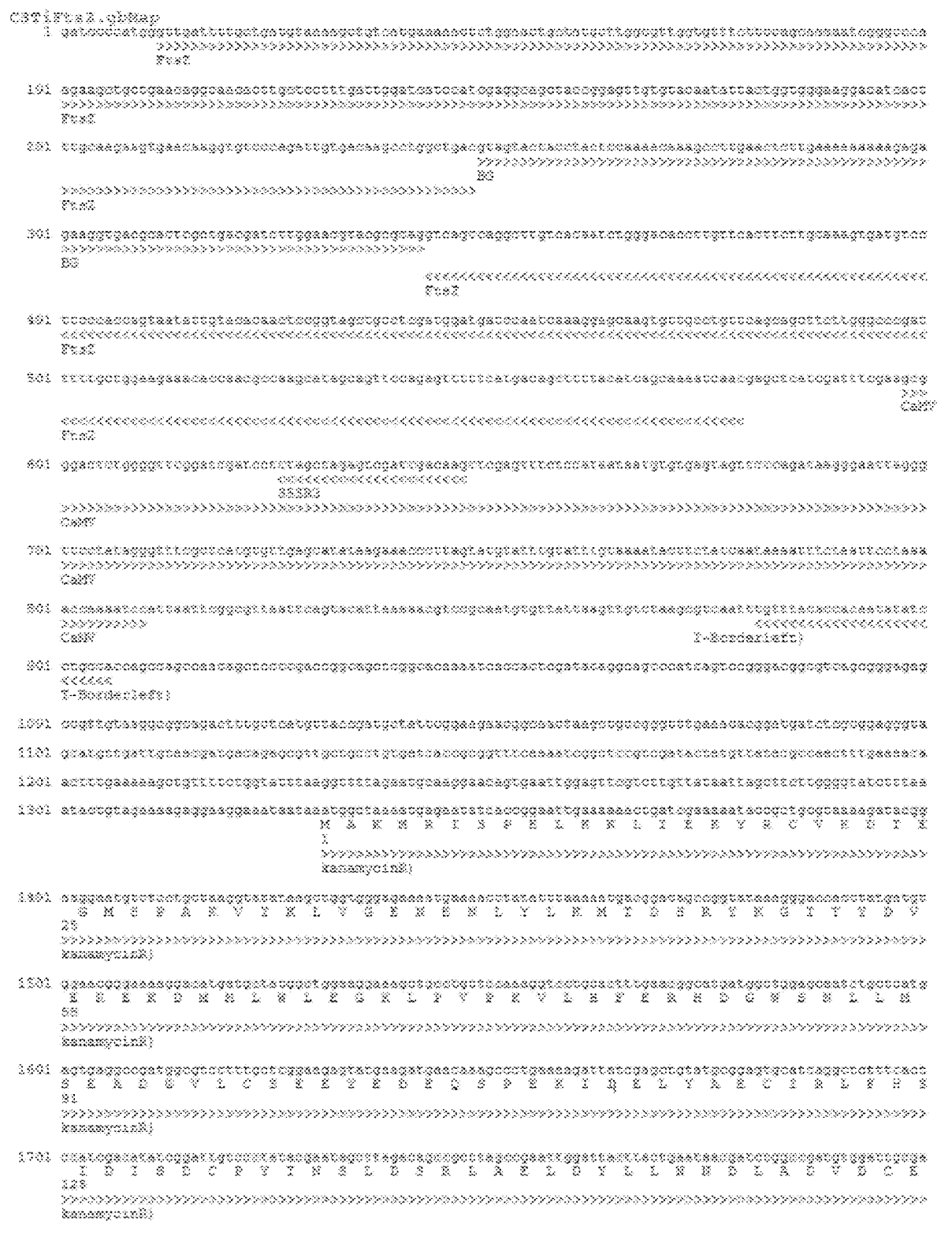
Figure 4B:
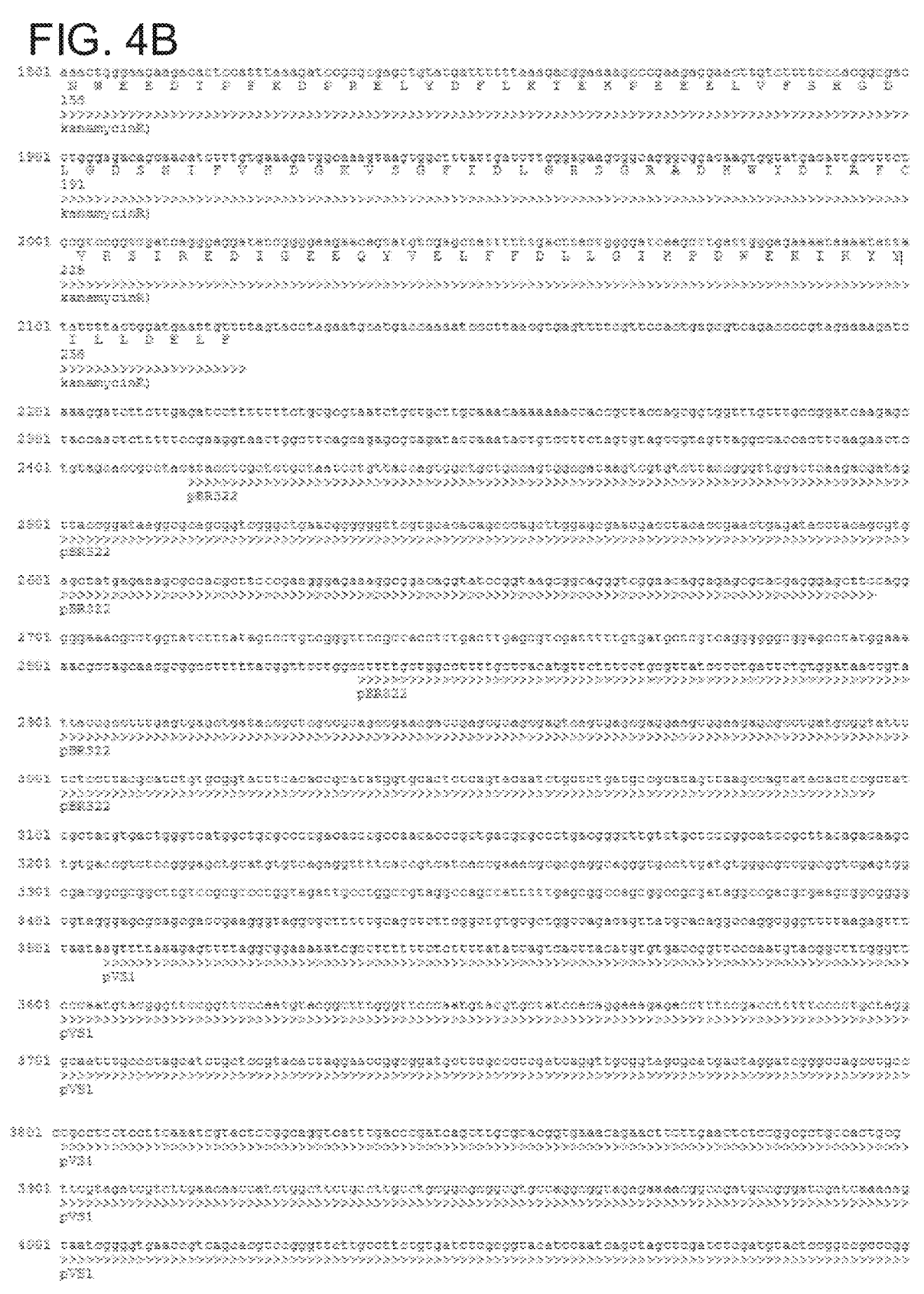
Figure 4C:
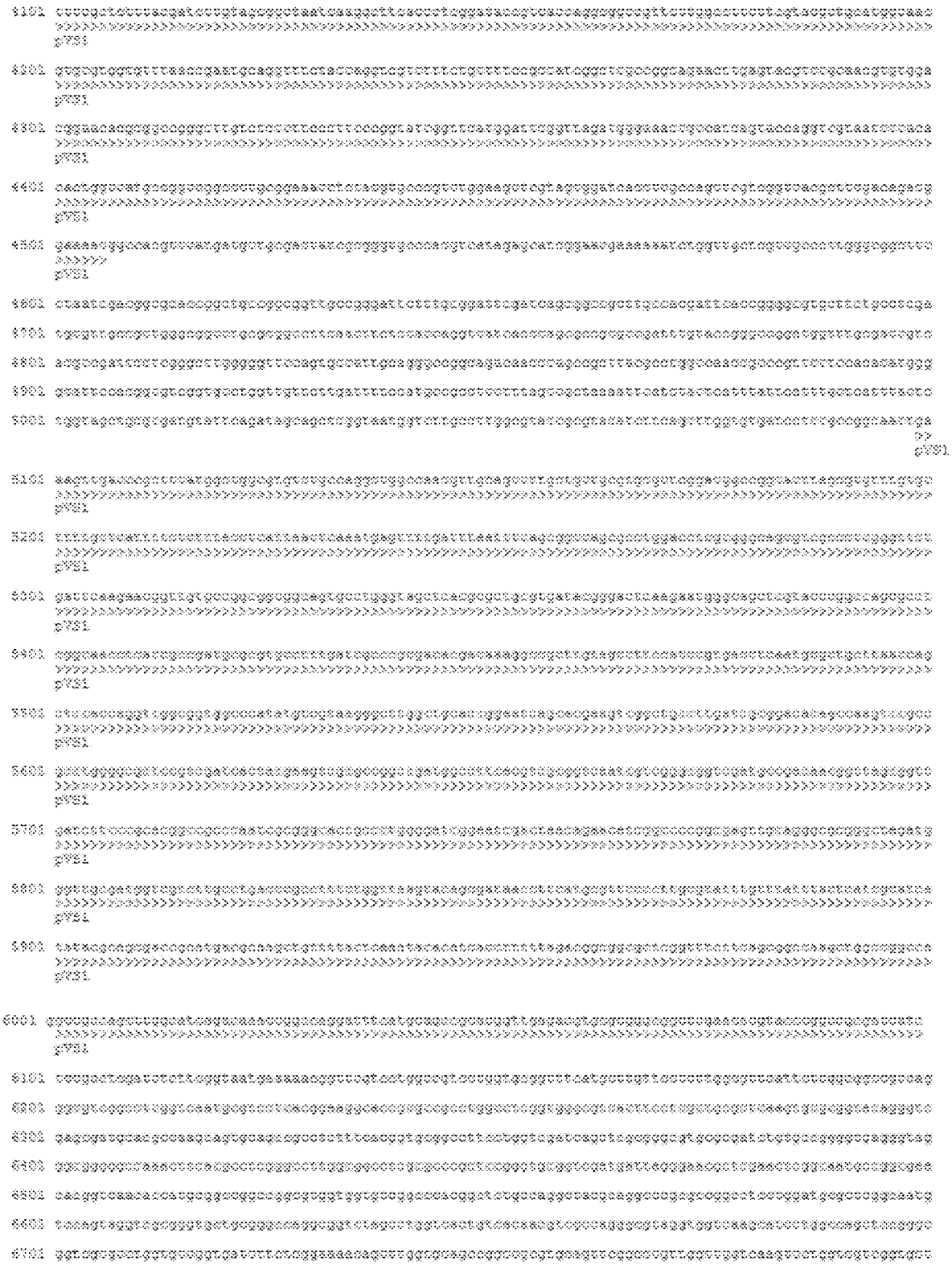
Figure 5:
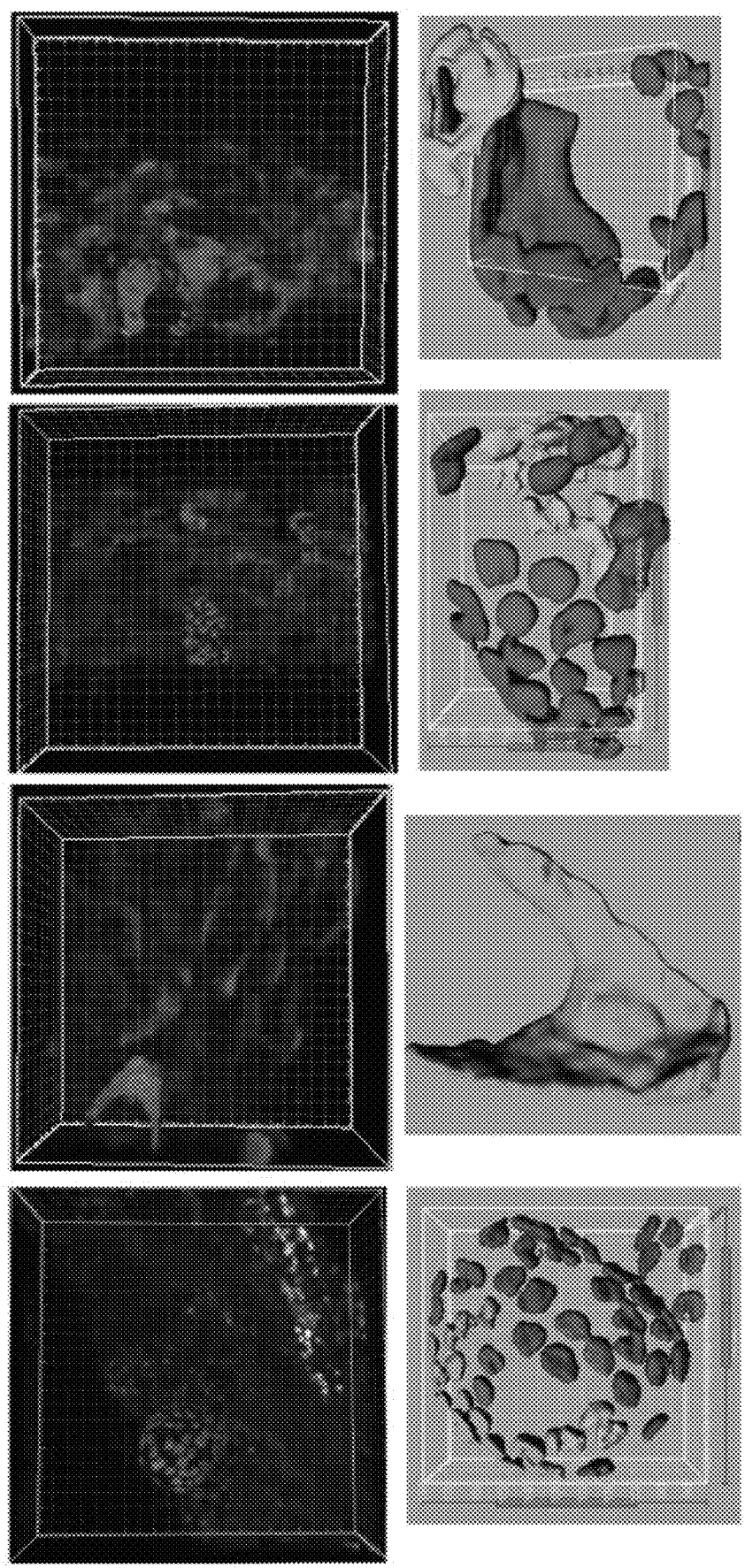
FIG. 5. *Arabidopsis* FtsZ1 mutant size classes. Top images are leaf cross sections from LSM confocal microscopy. Bottom images are 3-D surface images of chloroplasts with volume estimates. 3-D images were done using Imaris imaging software (BitPlane).

Further to FIG. 3, the below provides a description of all the component parts of the vector shown and descriptions of parts not shown. These elements are illustrated graphically in FIG. 4A-4D. Of the listed elements, is the sugarcane FtsZ1 sequence forward (12-248) and reverse (343-579) as these regions are specific to obtain RNA inhibition of FtsZ1; these sequences could be used in different nucleic acid contexts to similarly obtain inhibition of this gene/protein, to reduce chloroplast number/increase chloroplast size, and to provide increased biomass in a plant or plant part.

Genes of Interest
  Gene: FtsZ from *Saccharum officinarum*—Sense FtsZ exon (FtsZ 12 . . . 248) and antisense FtsZ exon (FtsZ 579 . . . 343) (Sugarcane Filamenting temperature sensitive mutant Z)
  Intron (BG\Intron 249 . . . 342): 4CL intron from *Paspalum notatum*—94 bp of 4-coumarate: CoA ligase (4CL) intron from bahia grass in between sense and antisense exons of gene of interest
  Terminator (CaMV\PolyA 598 . . . 810): T35S terminator from Cauliflower mosaic caulimovirus—T35S terminator is the poly A signal from CaMV; Feature 35SR3 647 . . . 626 is part of the terminator sequence
  Promoter (e35S 7412 . . . 8058): 35S CaMV promoter from Cauliflower mosaic caulimovirus—35S CaMV promoter from cauliflower mosaic virus controls expression of gene of interest
  Intron (HSP70\Intron 8063 . . . 8870): HSP70 intron from *Zea mays*—intron of heat shock protein 70 from maize Plant Selectable Marker Information (not Shown in FIG. 3)
  Promoter: ubiquitin from *Zea mays*—Ubiquitin promoter from maize controls the expression of marker gene
  Intron: ubiquitin intron from *Zea mays*—First intron of ubiquitin from maize
  Gene: npt II gene from *Escherichia coli*—Neomycin phosphotransferase II gene (AAA72847) is used as a marker during transformation
  Terminator: T35S terminator from Cauliflower mosaic caulimovirus—T35S terminator is the poly A signal from CaMV Components for Bacterial Growth
  kanamycin\(R) 1331 . . . 2122: bacterial selectable marker
  pBR322\ori 2416 . . . 2696: origin of replication, allows plasmid to be replicated in the bacteria. (pBP322 is the name of the plasmid backbone used to create this vector.)
  pBR322\bom 2836 . . . 3096: basis of mobility, allows for conjugation
  pVS1\rep 3506 . . . 4506: bacterial origin of replication
  pVS1\sta 5099 . . . 6099: stability region
  pUC57F 7387 . . . 7404 & M13F 7387 . . . 7404: primer regions for sequencing In certain embodiments, vector components other than those shown in FIG. 3 are contemplated. For example optional constitutive promotors can include: pathogen derived promotors such as 35S cauliflower mosaic virus and opine promoters (nos, ocs, mas); plant derived promoters such as Ubiquitin (Ubi), Actin (Act) and alcohol dehydrogenase (Adh); tissue specific promotors such as Rubisco small subunit (RbsS1) and Chlorophyll A/B binding protein (Cab) for leaf tissue expression, GmPRP2 (from soybean) for root tissue expression. If the gene of interest (for instance, any encoding one of the proteins in Table 1, or encoding a component of the chlorophyll biosynthetic pathway) is driven by a non-tissue specific promotor, all plastid types will be affected. In the current mutant we have there are no negative side effects observed. There could be a potential benefit to having larger plastids in root cells in that nitrogen assimilation could be increased.

In embodiments, additional or optional gene terminators are contemplated and can include NOS (opine synthesis pathway) for example. In embodiments, additional or optional plant specific selectable markers are contemplated and can include Glufosinate (bar gene), Neomycin phosphotransferase H (NPTII), hygromycin phosphotransferase (hpt), Gentamicin acetyltransferase, Bleomycin, phleomycin, streptomycin, spectinomycin, and mannose for example.

Although the methods and plants/plant parts described herein are exemplified using FtsZ1 inhibition, additional proteins involved in chloroplast divisional are contemplated for use herein in order to increase the biomass of plants. Examples of chloroplast divisional proteins are provided in Table 1.

TABLE 1

Proteins involved in chloroplast (cp) division.

| Protein | Proposed function | Mutant phenotype (in *Arabidopsis*) |
| --- | --- | --- |
| FtsZ1 | Assembles with FtsZ2 at mid-plastid contractile ring (the Z-ring) | large chloroplasts (cp), various sizes and numbers/cell |
| FtsZ2 | Assembles with FtsZ1 at mid-plastid contractile ring | 1-2 large cp/cell |
| ARC6 | Spans cp inner membrane, interacts with FtsZ2 | 1-2 mesophyll cell cps |
| PARC6 | Spans cp inner membrane, interacts with ARC3 to inhibit Z-ring assembly | Abnormal cp sizes and shapes |
| PDV1 | Localizes to cp inner membrane, regulates rate of cp division | Reduced cp numbers/cell. Cps have constriction in the middle |
| PDV2 | Localizes to cp inner membrane, regulates rate of cp division | Reduced cp numbers/cell. Phenotype is similar to ARC6 |
| DRP5B (ARC5) | Localizes to cp outer membrane (cytosolic side), outer membrane constriction | Dumbell shapes cps |

TABLE 1-continued

Proteins involved in chloroplast (cp) division.

| Protein | Proposed function | Mutant phenotype (in *Arabidopsis*) |
|---|---|---|
| PDR1 | Localizes to cp outer membrane (cytosolic side) | Not described |
| ARC3 | Part of Min system (positioning of division ring) Inhibits Z-ring formation at non-division locations by FtsZ1 and FtsZ2 interaction | Few, very large cps |
| MinD (ARC11) | Inhibits Z-ring formation at non-division locations | Heterogeneous cps and multiple Z rings in mesophyll cells |
| MinE (ARC12) | Believed to suppress ARC3 activity at mid-plastid division site | Heterogeneous cps and multiple Z rings in mesophyll cells |
| MCD1 | Part of Min system | Not described |
| MinC-like | Unknown | Not described |
| GC1 | Believed to be positive or negative regulator of cp division | Large cps |
| CLMP1 | Final cp separation | Plastids clump together |
| CLR | Cp segregation | Not described |

Information from Osteryoung & Pyke, *Annu Rev Plant Biol*, 65: 443-472, 2014; and from TAIR (on the World Wide Web at arabidopsis.org).

For RNAi to work most effectively, the inhibitory (hairpin loop) sequence needs to have high homology to the endogenous gene and thereby target its mRNA. Plastid division genes have been shown to be fairly well conserved across plant species, and it well within ordinary skill to identifying homologous regions. By way of example, the sugarcane FtsZ1 forward region (12-248) in the vector described herein that has 97% identity to corn, 95% to millet, 92% to Brachypodium, 91% to rice and 83% to soybean.

Though inhibition of gene expression (e.g., of FtsZ) is exemplified herein through RNAi, it will be understood by one of ordinary skill in the art that other methods can be used. For instance, mutagenesis techniques can be used to introduce specific or random changes in the targeted gene(s). Thus, EMS mutagenesis, fast-neutron mutagenesis, site-directed mutagenesis, and CRISPR/Cas9 mutational systems. By way of example, ethyl methanesulfonate (EMS; $C_3H_8SO_3$) is a way to induce chemical modification of nucleic acids. It produces random mutations in genetic material by nucleotide substitution. Mutagenized populations are screened for the phenotype of interest and backcrossed to parent to eliminate background mutations. Site-directed mutagenesis introduces mutations into the gene of interest on a plasmid. This mutated plasmid is then transformed into the plant of interest.

Targeted gene editing can be done using CRISPR/Cas9 technology (Saunders & Joung, *Nature Biotechnology*, 32, 347-355, 2014), and more generally crRNA-guided surveillance systems for gene editing. The FtsZ hairpin loop in the construct described herein would be substituted with a CRISPR cassette. Additional information about crRNA-guided surveillance complex systems for gene editing can be found in the following documents, which are incorporated by reference in their entirety: U.S. Application Publication No. 2010/0076057 (Sontheimer et al., TARGET DNA INTERFERENCE WITH crRNA); U.S. Application Publication No. 2014/0179006 (Feng, CRISPR-CAS COMPONENT SYSTEMS, METHODS AND COMPOSITIONS FOR SEQUENCE MANIPULATION); U.S. Application Publication No. 2014/0294773 (Brouns et al., MODIFIED CASCADE RIBONUCLEOPROTEINS AND USES THEREOF); and Sorek et al., *Annu. Rev. Biochem.* 82:273-266, 2013.

As recognized by those of skill in the art, elements of an expression vector may also beneficially be modified to suit the plant into which it is to be expressed. For instance, the vector or elements within it can be optimized for the target plant (e.g., for dicots versus monocots), using standard technology (e.g., through codon optimization programs, such as provided by GenScript; available online at genscript.com). The linker region (BG intron) might also be modified for particular target plants. Regulatory regions and promotors also can be changed to provide optimized expression in different plants.

In certain embodiments, in addition to reducing the number/increasing the size of chloroplasts it is also beneficial to reduce the level of chlorophyll. Decreased in chlorophyll levels can be obtained using the same type of technology used to increase chloroplast size (for instance, RNAi or CRISPR/Cas9). To decrease chlorophyll, one or more genes of the chlorophyll biosynthetic pathway are targeted, for instance specifically chlorophyll synthase, chlorophyllide a oxygenase, NADPH:protochlorophyllide oxidoreductase, divinyl-protochlorophyllide reductase, and enzymes of the magnesium chelatase complex (Mochizuki et al., *Trends Plant Sci.*, 15: 488-498, 2010). These two traits can be combined by creating a multi-gene construct containing all of the genes of interest, transforming plants with multiple plasmids containing the genes of interest, re-transformation of existing lines with additional genes, or crossing of high performing lines containing genes of interest.

EXAMPLES

The disclosure may be further understood by the following non-limiting examples.

Example 1

Isolation of Sugarcane FtsZ and Vector Construction

A total of 41 tentative consensus sequences (TCs) and ESTs of *Arabidopsis* (*Arabidopsis thaliana*), sorghum (*Sorghum bicolor*), maize (*Zea mays*), and sugarcane (*Saccharum officinarum*) homologous to FtsZ (Filamenting temperature sensitive mutant Z) were downloaded from the Gene Index Project (compbio.dfci.harvard.edu/tgi/) and the NCBI (ncbi.nlm.nih.gov/) websites. Primers were designed as ScFtsZF (SEQ ID NO: 2; 5'-CACCGATTCCCAAGCCCT-TATTA-3') and ScFtsZR (SEQ ID NO: 3: 5'-GCTT-TATGGGCGAGGGTTGCTG-3') using conserved region from multiple alignments of the downloaded sequences. In order to isolate a partial FtsZ sequence from sugarcane cultivar CP 88-1762 total RNA was extracted from 1 g of sugarcane leaves using the Trizol reagent (Life Technologies, Carlsbad, Calif.) following the manufacturer's instruction. After verification of total RNA quality and quantity by formaldehyde gel electrophoresis, a total of 1 µg total RNA was converted into cDNA with the iScript cDNA Synthesis kit (Bio-Rad, Hercules, Calif.). Diluted first strand cDNA was used as a template for the synthesis of the second strand cDNA with ScFtsZF and ScFtsZ primers designed as described above. PCR was performed in MyIQ thermocycler (BioRad, Hercules, Calif.) using Phusion® High-Fidelity DNA polymerase (New England Biolabs, Ipswich, Mass.) in accordance with manufacturer's instruction. The PCR reaction (25 µl) were denatured at 98° C. for 30 sec; followed by 30 cycles at 98° C. for 10 sec, 62° C. for 30 sec, 72° C. for 1 min, and a final extension cycle of 72° C. for 10 min. The PCR amplified partial sequence for FtsZ (904 bp) was confirmed by sequence analysis. The most conserved region with a length of 237 bp of this partial FtsZ sequence was used as a template to design a custom sequence including sense and antisense direction of 237 bp fragments of FtsZ partial sequence from *Saccharum* spp. Hybrids cv CP88 1762 separated by the 94 bp intron from *Paspalum notatum* 4-coumarate-CoA ligase (Fouad et al., *In Vitro Cell. Dev. Biol.-Plant,* 48:15-22, 2010). FtsZ RNAi vector was constructed by subcloning the custom sequence under transcriptional control of the 35S promoter from cauliflower mosaic virus (CaMV) with the HSP70 intron of *Zea mays* L. and the CaMV polyA signal.

Sugarcane transformation was done using biolistic gene transfer and direct embryogenesis as described in Taparia et al. (*In Vitro Cell. Dev. Biol.-Plant* 48:15-22, 2012). *Sorghum* transformation was done by *Agrobacterium tumefaciens* infiltration.

Example 2

Toward Improving Photosynthetic Efficiency in Sugarcane: An Unexpected Effect of Plastid Size on Plant Growth Sugarcane (*Saccharum* sp. Hybrids) and sorghum (*Sorghum bicolor*) are among the most productive plants in production making them ideal candidates for biofuel feedstocks. Despite their high photosynthetic rates they still falls short of the modeled theoretical C4 NADP-ME maximum. Modeling has shown that increases in potential yield can only be achieved by increasing the photosynthetic efficiency of conversion of intercepted solar energy.

One approach we are taking to reach this goal of photosynthetic improvement is to alter the light environment within the leaf by changing chloroplast size. Using RNAi, sugarcane lines with increased chloroplast size were developed and planted in a replicated field trial at our field site in Citra, Fla. in 2014. Under field conditions no significant difference in photosynthetic performance was observed, however there was a significant increase in biomass on both a fresh and dry weight basis. Lightsheet microscopy demonstrated a change in light penetration within the leaf, but not enough to account for the increase in biomass.

Figure 6:
FIG. 6. Vector construction used for transformation. Schematic map of minimal expression cassette for FtsZ RNAi. The inverted repeats of the 237 bp of FtsZ from *Saccharum* spp. Hybrids cv. CP88-1762 (sense; FtsZ-S, antisense; FtsZ-AS) separated by 94 bp of *Paspalum notatum* 4CL intron (BG-I) controlled by enhanced CaMV 35S promoter (35S-P) with HSP70 intron (HSP-I) and CaMV 35S polyA (CaMV-T).

FtsZ1 is a tubulin-like protein closely related to the bacterial protein FtsZ and has been shown to play a role in plastid division (Osteryoung & Vierling, *Nature,* 376, 473-474, 1995; Strepp et al., *Proc. Natl. Acad. Sci. USA,* 95, 4368-4373, 1998) by forming a contractile ring (the stromal Z ring) along the inner plastid membrane (FIG. 6). Altering FtsZ1 expression has a negative impact on plastid division resulting in changes in plastid size. This change in size is dose dependent, where a small decrease in FtsZ1 expression results in a slight increase in plastid size while in plants with a larger decrease in expression there is a significant increase in plastid size. In some instances, one single large plastid is present in a cell.

Transgene constructs were co-introduced with the selectable NPTII expression cassette into the commercially important sugarcane cultivar CP88-1762 by biolistic gene transfer. Transgenic plants were regenerated via direct or indirect embryogenesis following selection on geneticin containing media.

Results

Figure 7A:
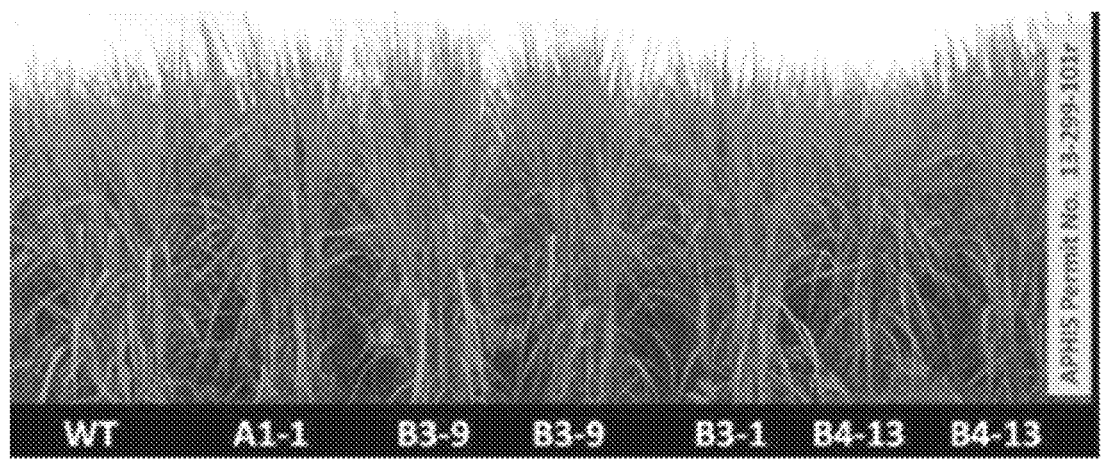
FIG. 7A-7B.
Figure 7B:
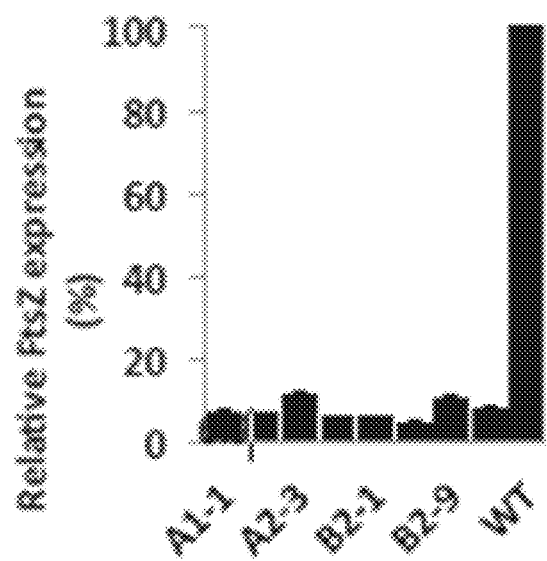

Lines with confirmed decreased expression of FtsZ1 were planted in a field trial at the University of Florida's Plant Science Research and Education Unit located in Citra, Fla. FIGS. 7A & 7B. Microscopic analysis of chloroplast size showed a 2-5 fold increase in the field grown plants, confirming that the gene knock down was altering plastid division.

TABLE 2

Sugarcane size measurements from two of the lines with changes in plastid size.

| Insert | Line | Est. Volume | Fold change |
|---|---|---|---|
| FtsZ RNAi | A1-1 | 200.72 | 5.101 |
| FtsZ RNAi | B2-9 | 104.587 | 2.658 |
| Parental | — | 39.348 | 1 |

Lines are independent transformation events.

Figure 8:
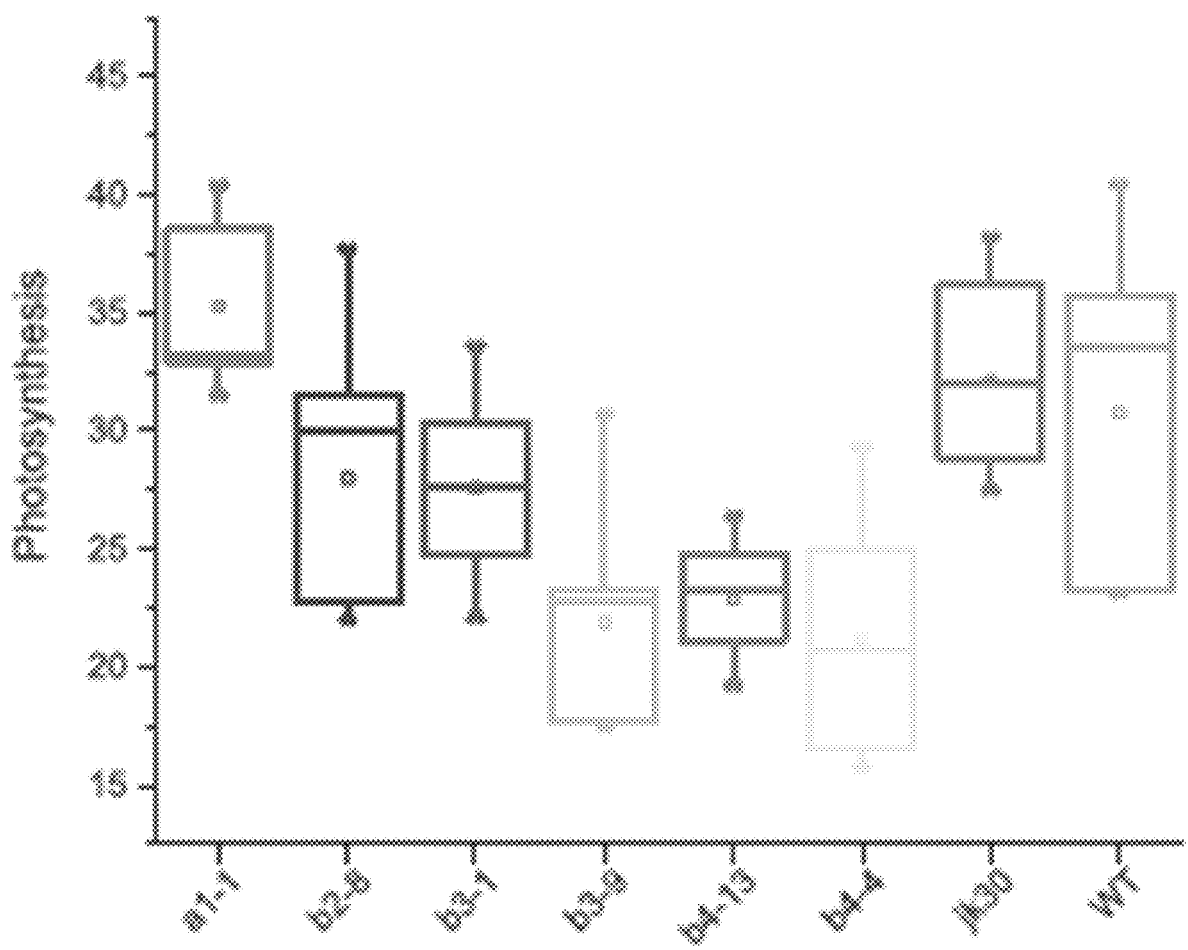
FIG. 8. Photosynthetic measurements of field grown FtsZ RNAi transgenic plants. Photosynthetic measurements were taken on fully expanded, non-senescing dewlap leaves at the top of the canopy using an open path gas exchange system equipped with a leaf chamber fluorometer (LI-6400, LI-COR, Lincoln, Nebr., USA) set to match the ambient growth conditions.

There were no significant differences in photosynthetic rates between the FtsZ1 RNAi lines and parental in the field nor where there changes in total leaf carbon and nitrogen. However, there were significant differences in biomass at the end of the season in two of the lines (A1-1 and JK30). FIG. 8

Figure 9A:
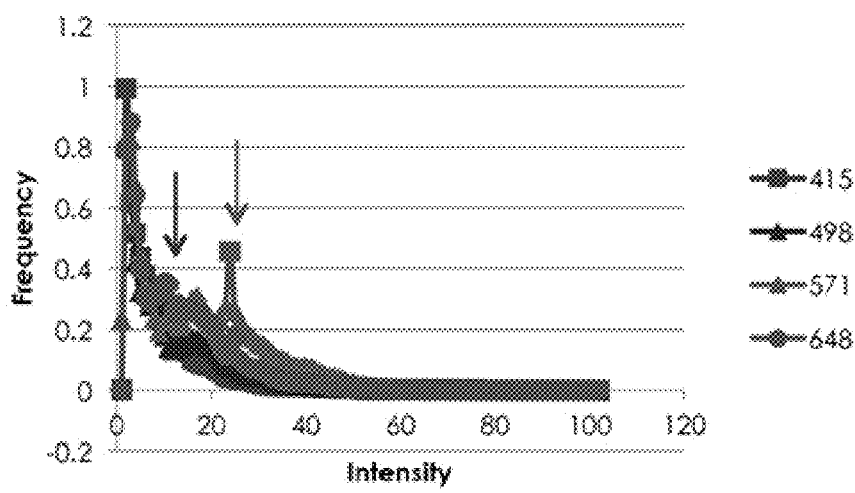
FIG. 9A-9C. Chlorophyll absorption profiles of wild type sugarcane, FtsZ RNAi transgenic sugarcane plants, and low chlorophyll transgenic plants. Comparison of chlorophyll absorption profiles between wild type (FIG. 9A), low chlorophyll (FIG. 9B) and FtsZ1 RNAi (FIG. 9C) plants at four wavelengths 405 nm, 488 nm, 561 nm, and 638 nm.
Figure 9B:
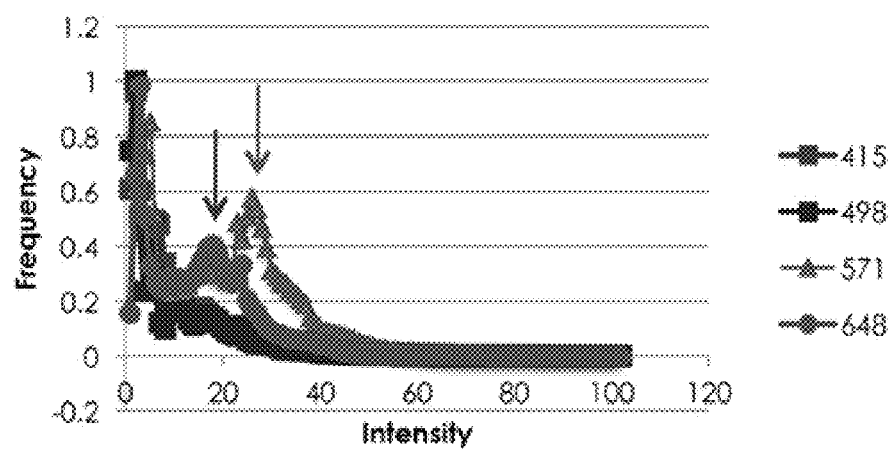
Figure 9C:
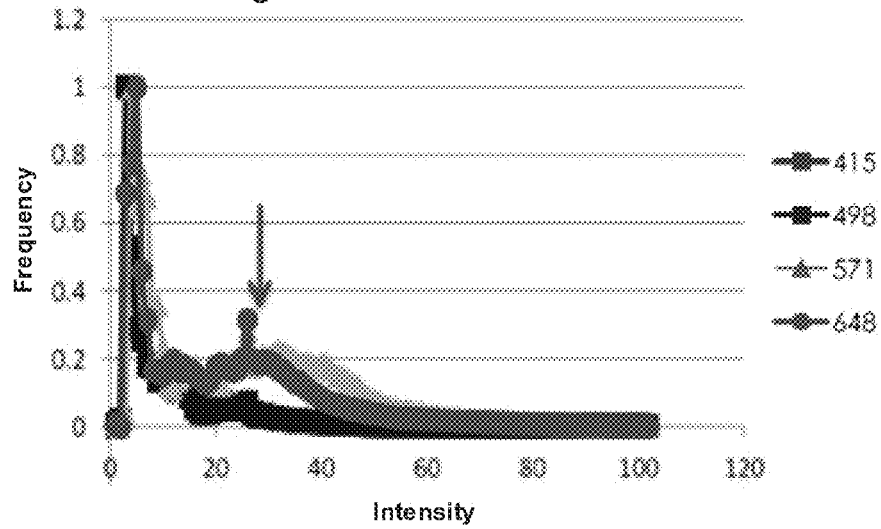
Figure 10A:
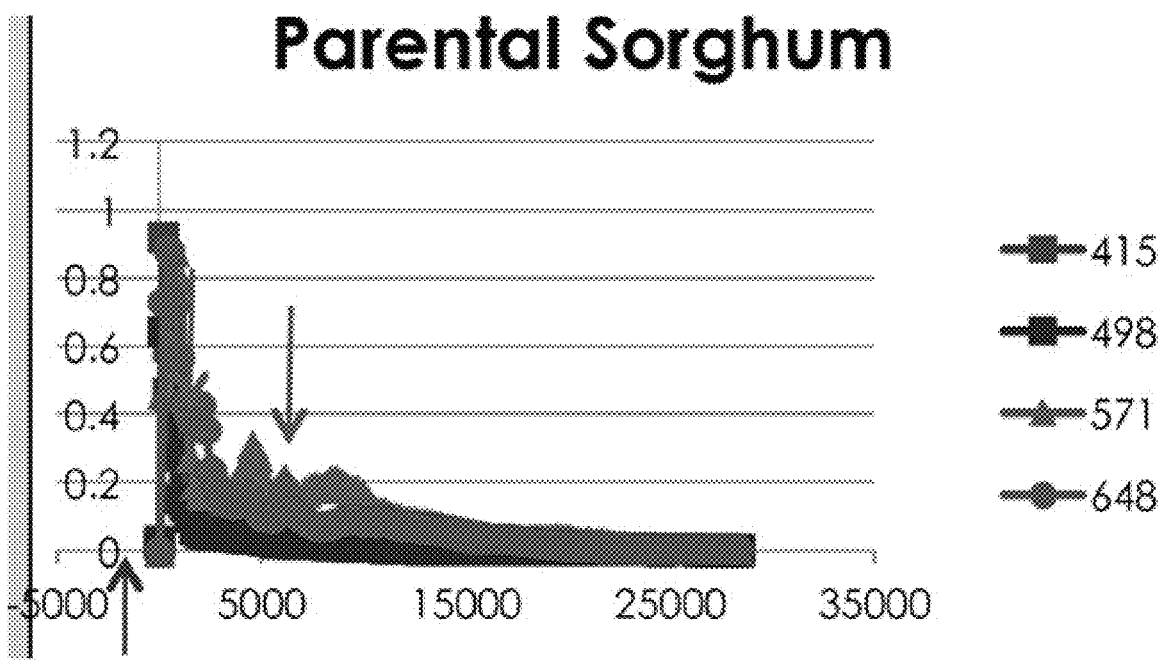
FIG. 10A-10B. Chlorophyll absorption profiles of wild type *sorghum* and low chlorophyll transgenic plants. Comparison of chlorophyll absorption profiles between wild type (FIG. 10A), low chlorophyll (FIG. 10B) plants were taken on a Zeiss light sheet microscope at four wavelengths 405 nm, 488 nm, 561 nm, and 638 nm.
Figure 10B:
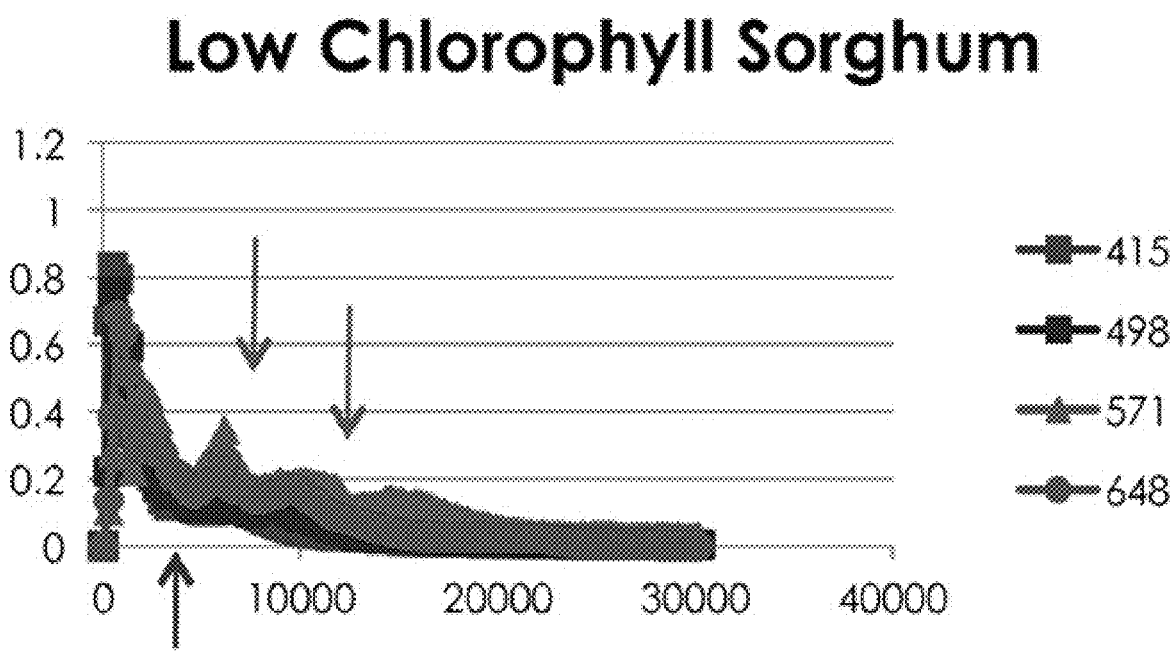

Using lightsheet microscopy, a shift in the light profile within the leaf is observed but not enough to account for the increase in biomass. FIG. 9A-9C (Sugarcane); FIG. 10A-10B (*Sorghum*)

The RNAi construct used in this Example is under the strong constitutive 35S promoter, and thus FtsZ1 expression will be knocked down in all tissues. Likewise, all plastid types will be impacted. A change in plastid size could alter the dynamics within the cell, potentially altering carbon and nitrogen assimilation and utilization. To that end, changes in nitrogen use efficiency (NUE) as well as changes in transient starch accumulation are currently being investigating in greenhouse grown plants.

Example 3

The Impact of Increased Plastid Size on Plant Growth and Development

In this example, we looked at the impact of increased plastid size on the growth development in two annual plants, the C3 dicot *Arabidopsis thaliana* and the C4 monocot *Sorghum bicolor.*

Arabidopsis FtsZ1 T-DNA insertion mutants were obtained from the Arabidopsis Biological Resource Center (abrc.osu.edu/). The reported changes to chloroplast size and number were confirmed using lightsheet microscopy (Zeiss Lightsheet Z1).

Figure 11:
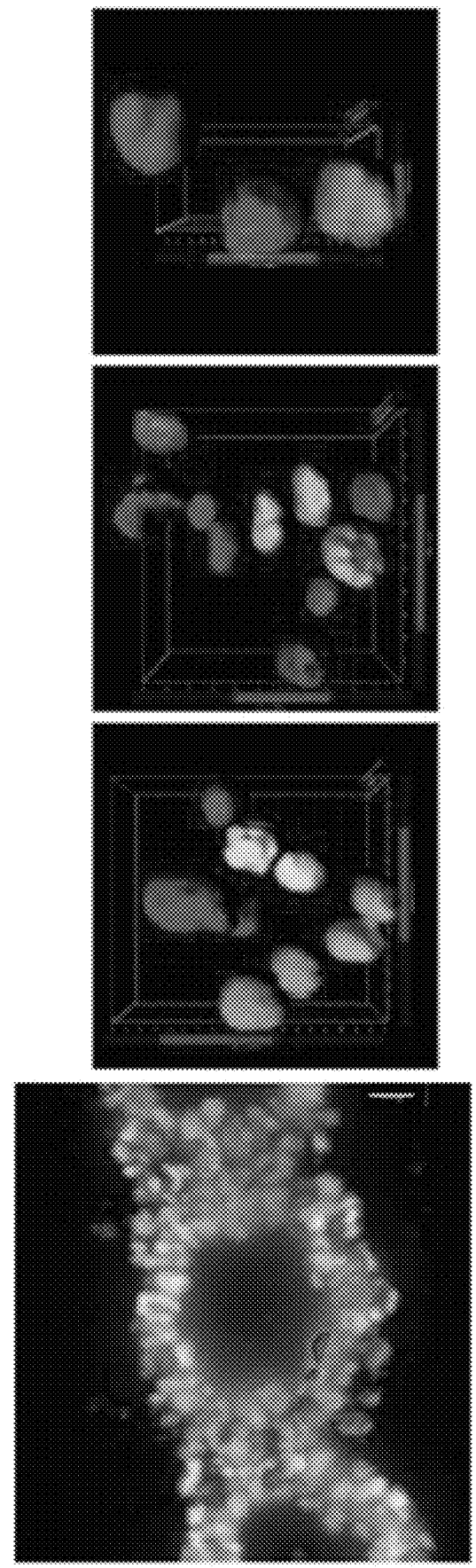
FIG. 11. *Sorghum* FtsZ1 mutant size classes. Leftmost image are leaf cross sections from Light Sheet microscopy. Remaining images are 3-D surface images of chloroplasts with volume estimates (Wild type, line 5a, and line 3b). 3-D images were made using Imaris imaging software (BitPlane).
Figure 12A:
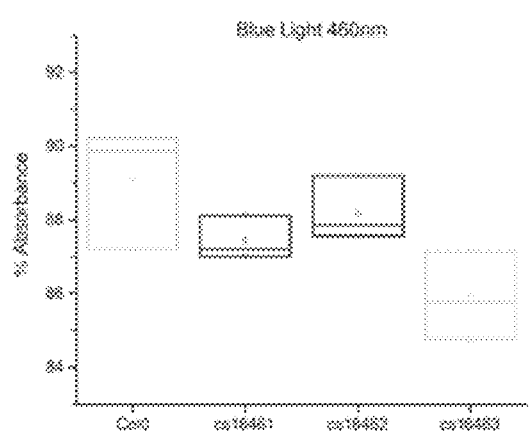
FIG. 12A-12D. Measurement of red and blue light absorbed or reflected by *Arabidopsis* plants with differing chloroplast sizes. Leaf optic measurements were taken using a leaf spectrophotometer (Ocean Optics).
Figure 12B:
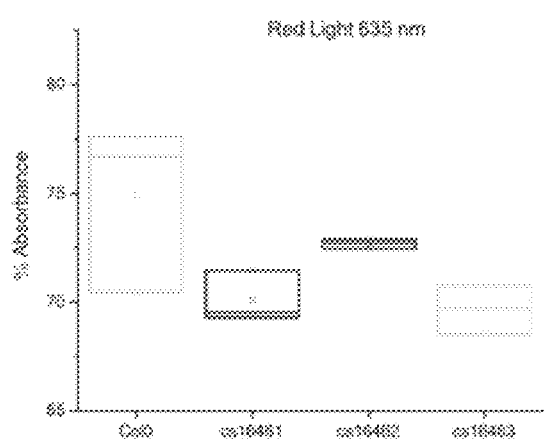
Figure 12C:
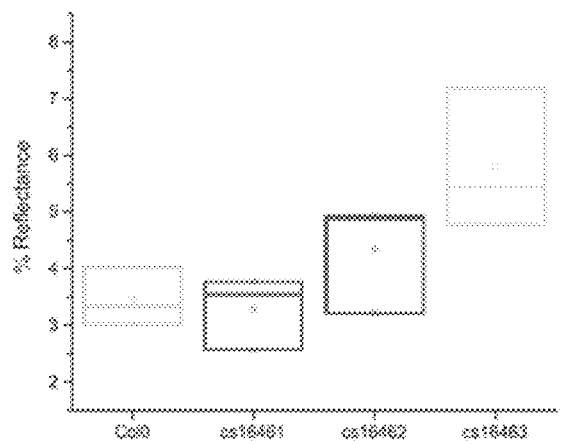
Figure 12D:
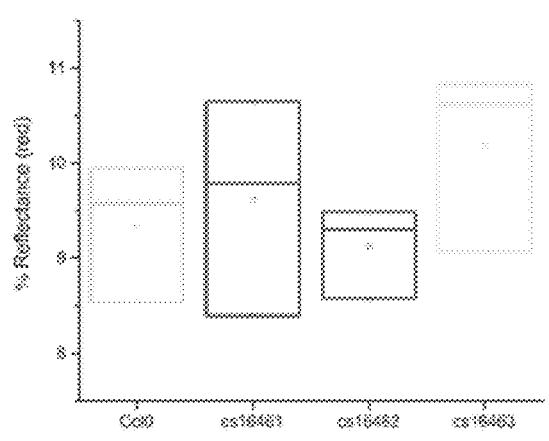
Figure 13A:
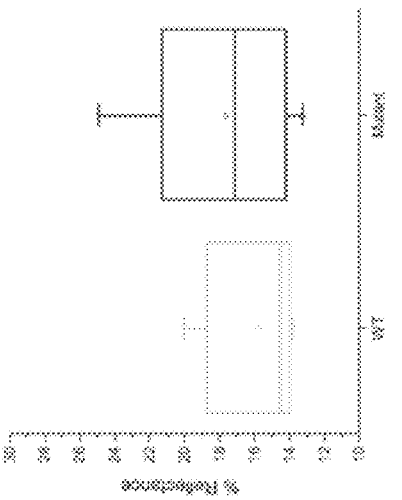
FIG. 13A-13E. Measurement of light properties of wild type and FtsZ RNAi transgenic *Sorghum* plants. Leaf optic measurements were taken using a leaf spectrophotometer (Ocean Optics).
Figure 13B:
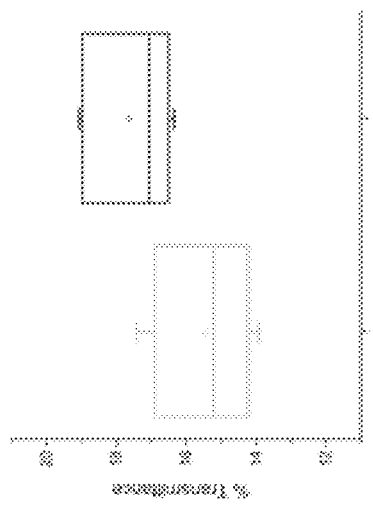
Figure 13C:
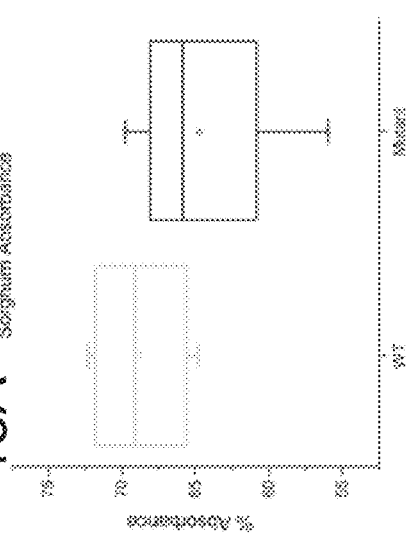
Figure 13D:
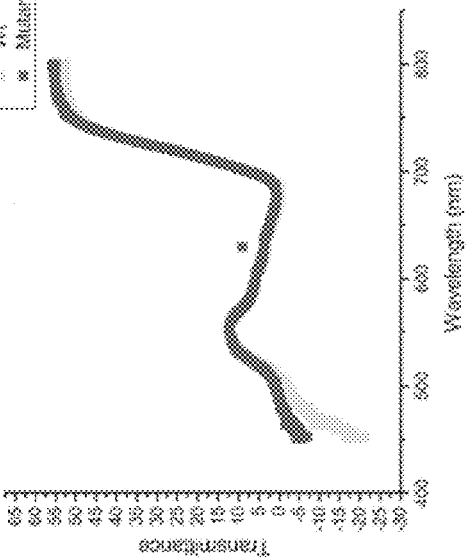
Figure 13E:
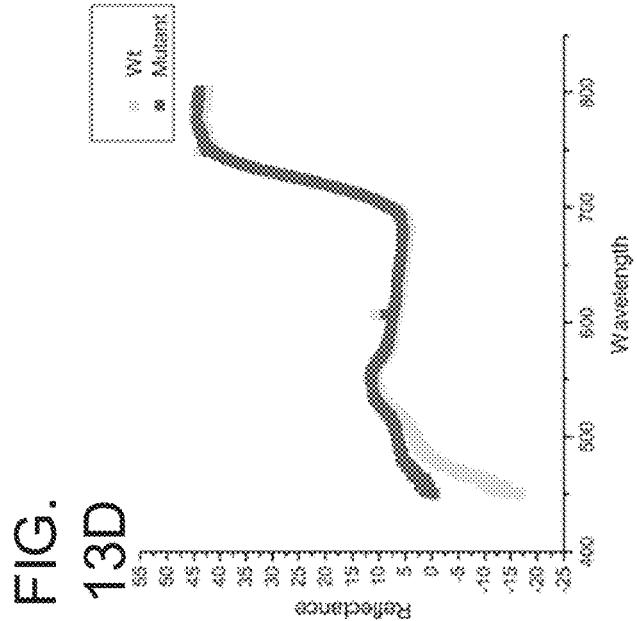
Figure 14A:
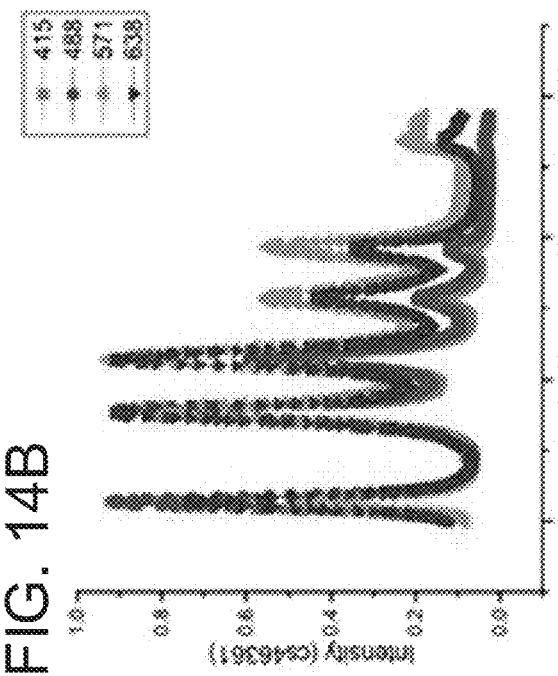
FIG. 14A-14D. Chlorophyll absorption profiles of wild type and chloroplast size mutants of *Arabidopsis*. Comparison of chlorophyll absorption profiles between wild type (FIG. 14A), Cs46361 (FIG. 14B), Cs46362 (FIG. 14C), and Cs46363 (FIG. 14D) plants at four wavelengths 405 nm, 488 nm, 561 nm, and 638 nm.
Figure 14B:
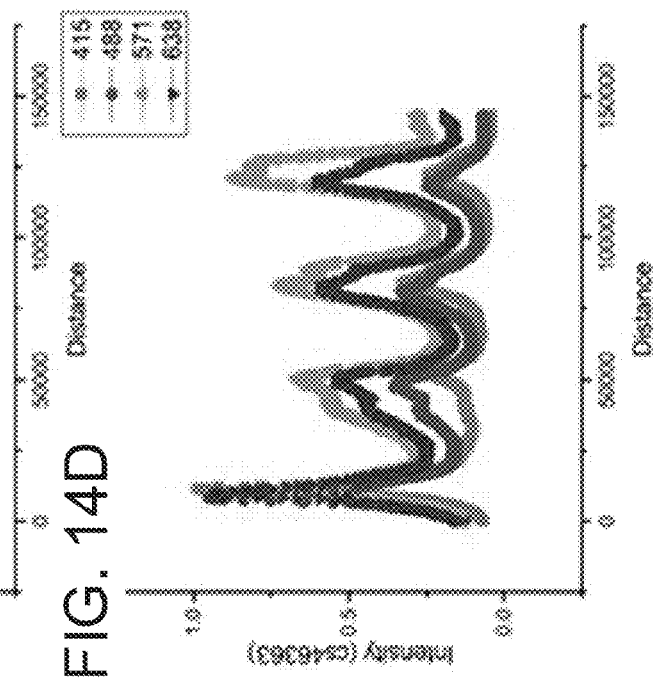
Figure 14C:
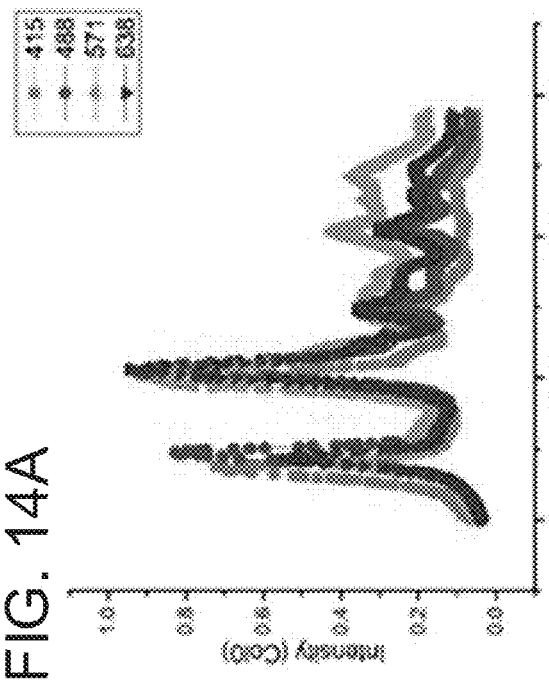
Figure 14D:
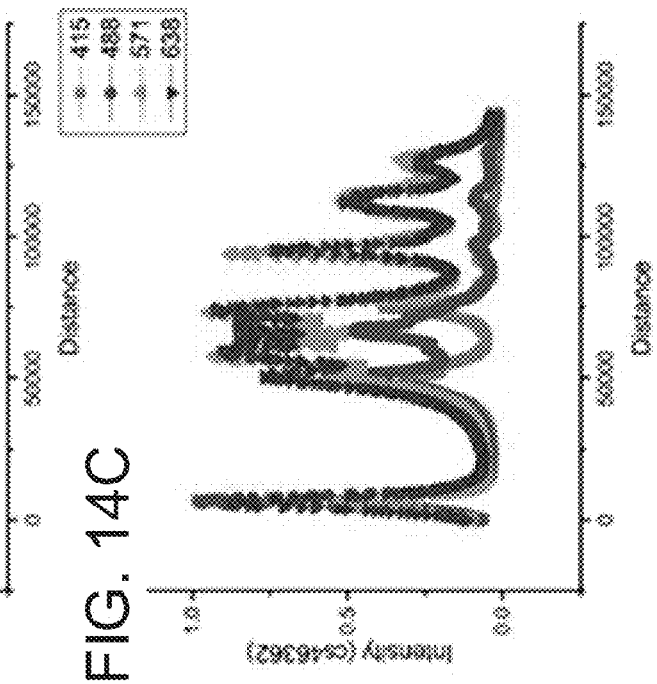

FtsZ1 expression was knocked down with RNAi to increase sorghum plastid size. Two lines with a 2- and 5-fold increase in chloroplast size have been identified, line AS and B9, respectively. (FIG. 11; Table 3)

TABLE 3

Sorghum size measurements from four independent transformation events.

| ID | Volume average ($\mu m^3$) | Observations |
|---|---|---|
| ZG342-1-5a | 922.77 | irregular shapes |
| ZG354-1-21a | 1327.68 | irregular shapes, heterogeneous sizes |
| ZG354-3-9a | 420.95 | slightly larger |
| ZG354-4-14a | | irregular shapes |
| parental | 345.51 | |

Changes in light absorbance was measured with an integrating sphere (Jaz spectroclip, OceanOptics).

Measurement of light absorbed or reflected by an Arabidopsis leaf (n=5) with an integrating sphere. Boxes represent integrated area under graph. (FIG. 12A-12D)

Measurement of light transmitted or reflected through a sorghum leaf (n=4) with an integrating sphere. Top panels represent integrated area under the graphs, bottom two are average traces. (FIG. 13A-13E)

Changes to the light movement within the leaves examined using the lightsheet microscope. Leaf sections were mounted and the intensity of chlorophyll autofluorescence was measured (LP filter 600-700 nm). Four excitation wavelengths were used: 415 nm, 488 nm, 571 nm, and 638 nm Fluorescence intensity was measured using the "Profiles" option in Zen blue software (Zeiss). Intensity was normalized and plotted using OriginPro (OriginLab).

Measurements of light path through an Arabidopsis leaf (n=5). In all three of the mutant lines, green and red light reached deeper into cell layers. (FIG. 14A-14D)

Figure 15A:
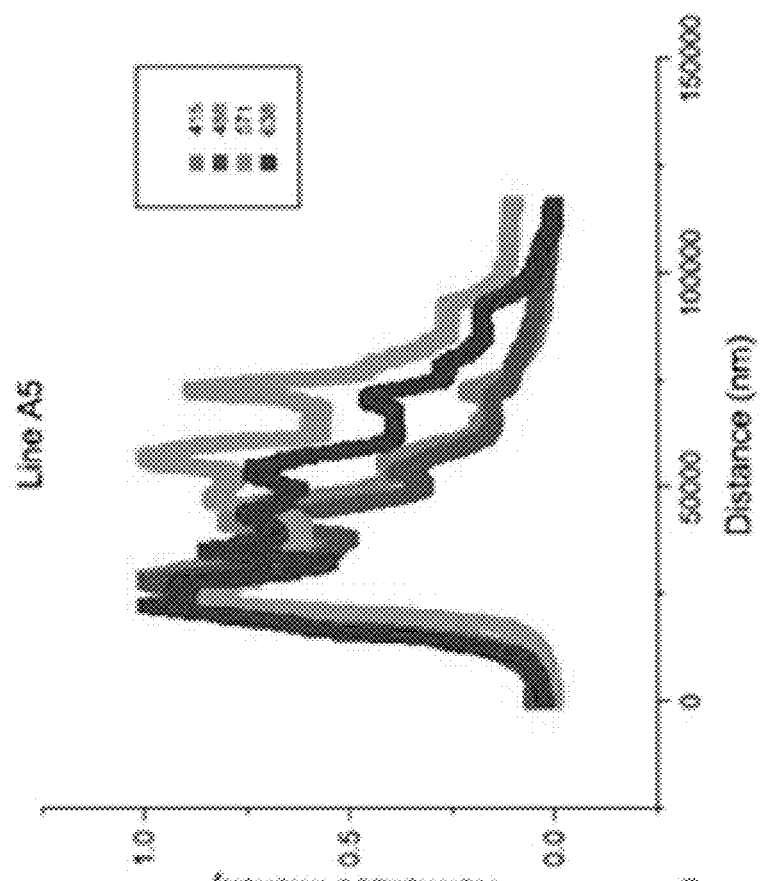
FIG. 15A-15B. Chlorophyll absorption profiles of wild type and FtsZ RNAi transgenic of *sorghum*. Comparison of chlorophyll absorption profiles between wild type (FIG. 15A) and line 5A (FIG. 15B) plants were taken on a Zeiss light sheet microscope at four wavelengths 405 nm, 488 nm, 561 nm, and 638 nm.
Figure 15B:
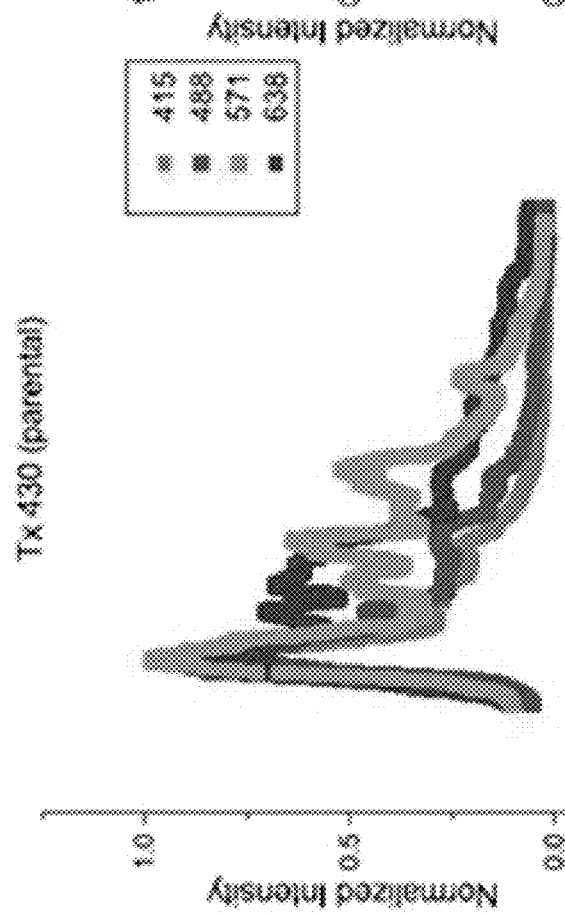

Measurement of light path through a sorghum leaf (n=4) using light sheet microscopy. Similar to what was seen in Arabidopsis, sorghum plants with increased chloroplast sizes had more light, specifically red and green wavelengths, going deeper into the leaf. (FIG. 15A-15B)

Figure 16A:
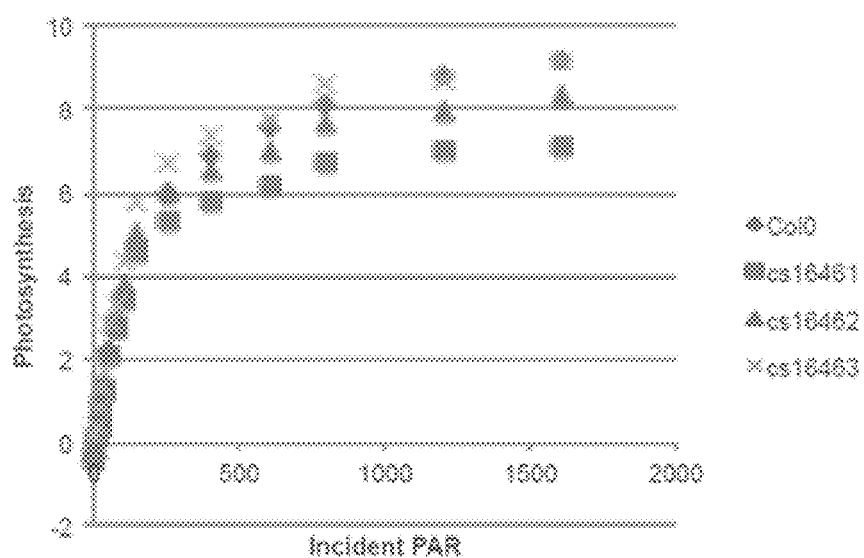
FIG. 16A-16C. Photosynthetic rates of wild type and chloroplast size mutants of *Arabidopsis*. Light response curves were taken to determine if the chloroplast mutants had similar rates of CO2 assimilation across different light levels. Net photosynthetic rates was plotted by incident PAR (FIG. 16A) and corrected for absorbed PAR (FIG. 16B). Net photosynthetic rates were also measured at varying concentrations of carbon dioxide and plotted against calculated substomatal carbon dioxide concentration (FIG. 16C) to determine if the plants were limited by Rubisco or electron transport.
Figure 16B:
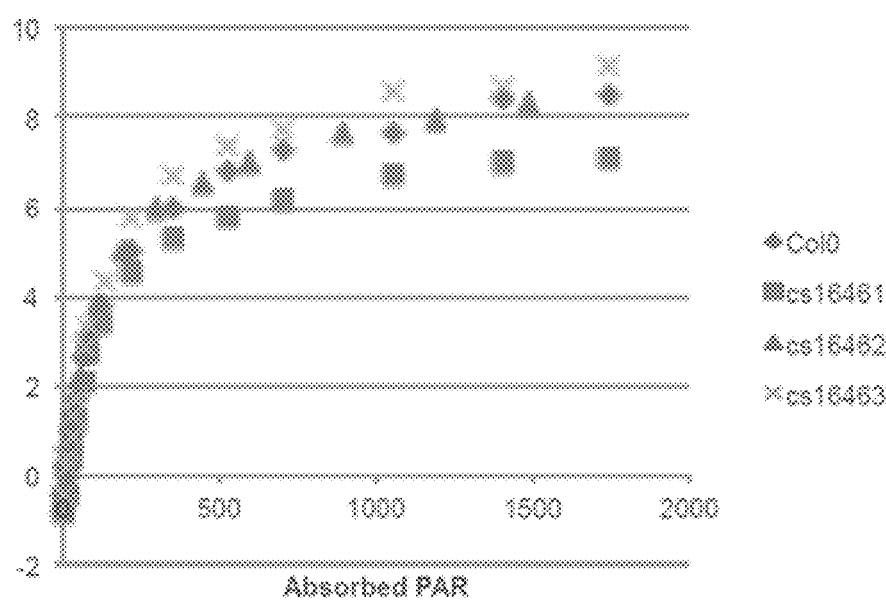
Figure 16C:
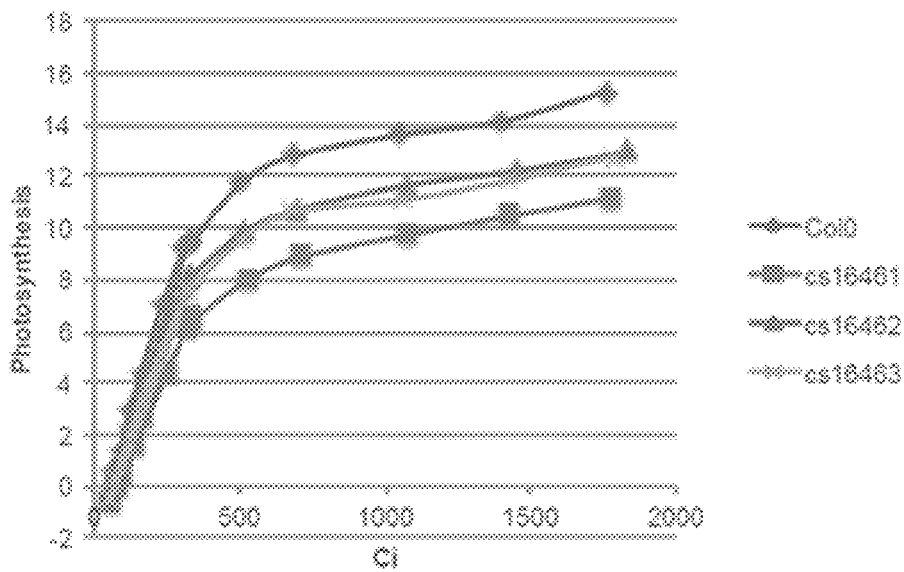
Figure 17A:
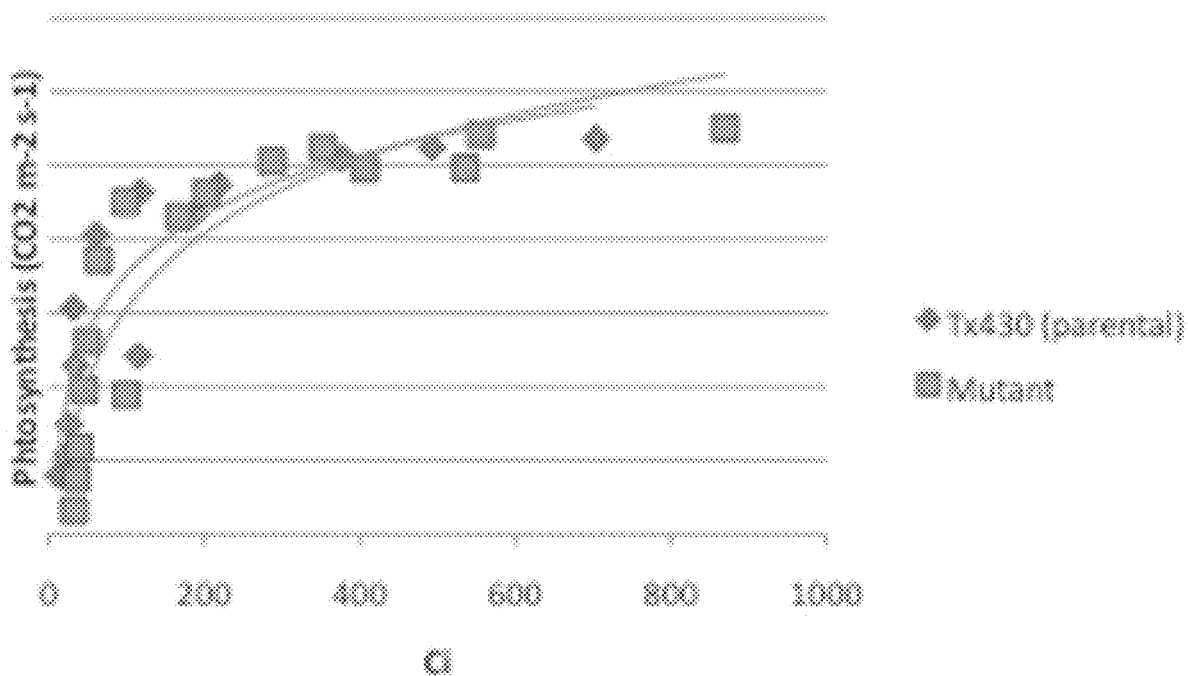
FIG. 17A-17B. Photosynthetic rates of wild type and FtsZ RNAi transgenics of *sorghum*. Net photosynthetic rates were measured at varying concentrations of carbon dioxide and plotted against calculated substomatal carbon dioxide concentration (FIG. 17A) to determine if the plants were limited by Rubisco or electron transport. Light response curves were taken to determine if the chloroplast mutants had similar rates of $CO_2$ assimilation across different light levels. Net photosynthetic rates was plotted by incident PAR (FIG. 17B).
Figure 17B:
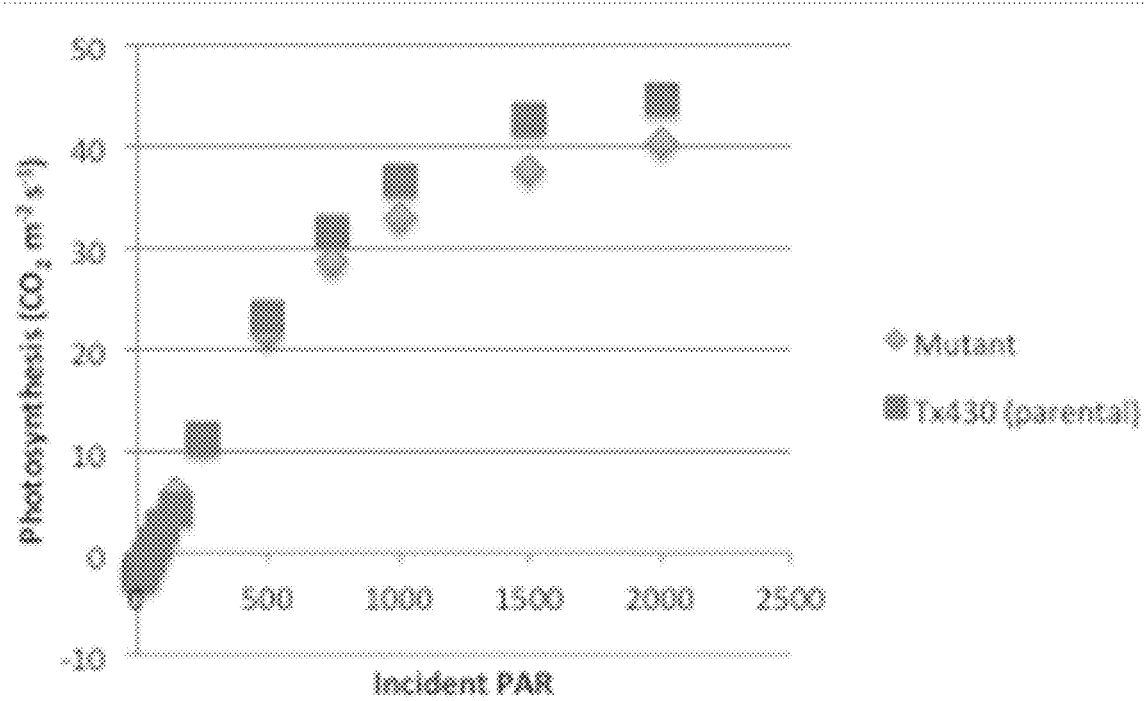

The impact of the increased light environment on photosynthesis was also examined in these lines. The only significant difference in photosynthesis based on incident PAR was between the wild type line and the single chloroplast line CS16461. The significance went away when plotted against absorbed PAR. (FIG. 16A-16C; FIG. 17A-17B)

Growth of both Arabidopsis and sorghum are not significantly impacted by the increase in chloroplast size and subsequent change in light absorption. Nor is there a difference in fresh or dry weigh of leaves. There was a significant difference in sorghum stalk fresh weight that went away upon drying. (FIG. 18A-18D)

There is an apparent difference in transition to flowering in both Arabidopsis and sorghum, where the lines with larger chloroplast flower earlier. This is seen in both long and short day conditions in Arabidopsis and in multiple lines of sorghum both in the greenhouse and field.

Example 4

Persistence of Increased Biomass

This example investigates the persistence of increased biomass in the second ratoon of sugarcane plants described in Examples 1-3.

As described above, in 2014 an increase in both photosynthetic rate (net assimilation) and biomass was observed in sugarcane lines transformed with FtsZ1 RNAi construct. The aboveground biomass of these lines was harvested and the plants were allowed to overwinter in the field. These plants (second ratoon) survived the winter and grew during the 2015 field season. The decrease in FtsZ1 gene expression was confirmed (FIG. 19). Photosynthetic rates (FIG. 20) and end of season biomass (FIG. 21) were again measured in 2015. An increase in both end of season biomass (fresh weight) and photosynthesis in the lines with increased chloroplast size, demonstrating the reproducibility and persistence of this trait in sugarcane.

In the 2015 field season, the amount of light reflected off the leaves as well as light transmitted through leaves was measured using a leaf spectrophotometer (FIG. 22A-22D). As chloroplast size increase, a sieve effect can possibly occur allowing more light the pass through the upper canopy leaves. In sugarcane leaves with large chloroplast, more light in the blue and shortwave near infra-red wavelengths were transmitted through the leaves with a concomitant decrease in reflectance at those wavelengths.

This disclosure provides methods of methods of generating plants with higher biomass production, through increasing chloroplast size/decreasing chloroplast number (e.g., by altering expression of one or more genes involved with plastid division, such as FtsZ1); and optionally decreasing chlorophyll level (e.g., by altering expression of magnesium chelatase and/or chlorophyll synthase). The disclosure further provides plants and plant parts produced through such methods. It will be apparent that the precise details of the methods described may be varied or modified without departing from the spirit of the described invention. We claim all such modifications and variations that fall within the scope and spirit of the claims.

We claim:

1. A method of producing a plant having increased biomass accumulation relative to a wild-type plant, comprising:

introducing into a plant cell a nucleic acid construct that reduces expression of a FtsZ1 gene to produce a transformed plant cell, wherein the construct is an RNAi construct that targets the FtsZ1 gene for RNAi silencing;

wherein the nucleic acid construct comprises nucleic acid sequences that have at least 80% identity to positions 12-248 and 343-579 of SEQ ID NO: 1;

regenerating a plant from the transformed plant cell;

measuring the fresh and or dry weight of the regenerated plant to determine biomass; and selecting for a regenerated plant with increased biomass as determined by the measuring step, wherein the increase in biomass is relative to that of a control plant grown under the same conditions and wherein the plant has reduced expression of FtsZ1 compared with the control plant.

2. The method of claim 1, further comprising reducing the level of chlorophyll expression in the regenerated plant by inhibiting expression of magnesium chelatase and/or chlorophyll synthase.

3. The method of claim 1, wherein the plant is a monocot.

4. The method of claim 3, wherein the monocot is one of corn, sorghum, sugarcane, *Miscanthus*, switchgrass, *Setaria*, and cordgrass.

5. The method of claim 1, wherein the plant is a dicot.

6. The method of claim 5, wherein the dicot is one of soybean, cotton, tobacco, pepper, potato, and tomato.

7. The method of claim 1, wherein the nucleic acid construct comprises nucleic acid sequences with 100% identity to positions 12-248 and 343-579 of SEQ ID NO: 1.

* * * * *

SEQUENCE LISTING

```
<160> NUMBER OF SEQ ID NOS: 4

<210> SEQ ID NO 1
<211> LENGTH: 8872
<212> TYPE: DNA
<213> ORGANISM: Artificial Sequence
<220> FEATURE:
<223> OTHER INFORMATION: Plasmid

<400> SEQUENCE: 1
```

```
gatccccatg ggttgatttt gctgatgtaa aagctgtcat gaaaaactct ggaactgcta      60
tgcttggcgt tggtgtttct tccagcaaaa atcgggccca agaagctgct gaacaggcaa     120
cacttgctcc tttgattgga tcatccatcg aggcagctac cggagttgtg tacaatatta     180
ctggtgggaa ggacatcact ttgcaagaag tgaacaaggt gtcccagatt gtgacaagcc     240
tggctgacgt agtactacct actccaaaac aaagccttga actcttgaaa aaaaagaga      300 gaaggtgacg cactcgctga cgatcttgga acgtacgcgc aggtcagcca ggcttgtcac     360
aatctgggac accttgttca cttcttgcaa agtgatgtcc ttcccaccag taatattgta     420
cacaactccg gtagctgcct cgatggatga tccaatcaaa ggagcaagtg ttgcctgttc     480
agcagcttct tgggcccgat ttttgctgga agaaacacca acgccaagca tagcagttcc     540
agagtttttc atgacagctt ttacatcagc aaaatcaacg agctcatcga tttcgaagcg     600
ggactctggg gttcggatcg atcctctagc tagagtcgat cgacaagctc gagtttctcc     660
ataataatgt gtgagtagtt cccagataag ggaattaggg ttcctatagg gtttcgctca     720
tgtgttgagc atataagaaa ccccttagtat gtatttgtat ttgtaaaata cttctatcaa     780
taaaatttct aattcctaaa accaaaatcc attaattcgg cgttaattca gtacattaaa     840
aacgtccgca atgtgttatt aagttgtcta agcgtcaatt tgtttacacc acaatatatc     900
ctgccaccag ccagccaaca gctccccgac cggcagctcg gcacaaaatc accactcgat     960
acaggcagcc catcagtccg ggacggcgtc agcgggagag ccgttgtaag gcggcagact    1020
ttgctcatgt taccgatgct attcggaaga acggcaacta agctgccggg tttgaaacac    1080
ggatgatctc gcggagggta gcatgttgat tgtaacgatg acagagcgtt gctgcctgtg    1140
atcaccgcgg tttcaaaatc ggctccgtcg atactatgtt atacgccaac tttgaaaaca    1200
actttgaaaa agctgttttc tggtatttaa ggttttagaa tgcaaggaac agtgaattgg    1260
agttcgtctt gttataatta gcttcttggg gtatctttaa atactgtaga aaagaggaag    1320
gaaataataa atggctaaaa tgagaatatc accggaattg aaaaaactga tcgaaaaata    1380
ccgctgcgta aaagatacgg aaggaatgtc tcctgctaag gtatataagc tggtgggaga    1440
aaatgaaaac ctatatttaa aaatgacgga cagccggtat aaagggacca cctatgatgt    1500
ggaacgggaa aaggacatga tgctatggct ggaaggaaag ctgcctgttc caaaggtcct    1560
gcactttgaa cggcatgatg gctggagcaa tctgctcatg agtgaggccg atggcgtcct    1620
ttgctcggaa gagtatgaag atgaacaaag ccctgaaaag attatcgagc tgtatgcgga    1680
gtgcatcagg ctctttcact ccatcgacat atcggattgt ccctatacga atagcttaga    1740
cagccgctta gccgaattgg attacttact gaataacgat ctggccgatg tggattgcga    1800
aaactgggaa gaagacactc catttaaaga tccgcgcgag ctgtatgatt ttttaaagac    1860
ggaaaagccc gaagaggaac ttgtcttttc ccacggcgac ctgggagaca gcaacatctt    1920
tgtgaaagat ggcaaagtaa gtggctttat tgatcttggg agaagcggca gggcggacaa    1980
gtggtatgac attgccttct gcgtccggtc gatcaggag gatatcgggg aagaacagta     2040
tgtcgagcta ttttttgact tactggggat caagcctgat tgggagaaaa taaaatatta    2100 tatttactg gatgaattgt tttagtacct agaatgcatg accaaaatcc cttaacgtga     2160
gttttcgttc cactgagcgt cagaccccgt agaaaagatc aaaggatctt cttgagatcc    2220 ttttttttctg cgcgtaatct gctgcttgca aacaaaaaaa ccaccgctac cagcggtggt    2280
ttgtttgccg gatcaagagc taccaactct ttttccgaag gtaactggct tcagcagagc    2340
gcagatacca atactgtcc ttctagtgta gccgtagtta ggccaccact tcaagaactc     2400
```

```
tgtagcaccg cctacatacc tcgctctgct aatcctgtta ccagtggctg ctgccagtgg   2460
cgataagtcg tgtcttaccg ggttggactc aagacgatag ttaccggata aggcgcagcg   2520
gtcgggctga acgggggtt cgtgcacaca gcccagcttg gagcgaacga cctacaccga    2580
actgagatac ctacagcgtg agctatgaga aagcgccacg cttcccgaag ggagaaaggc   2640
ggacaggtat ccggtaagcg gcagggtcgg aacaggagag cgcacgaggg agcttccagg   2700
gggaaacgcc tggtatcttt atagtcctgt cgggtttcgc cacctctgac ttgagcgtcg   2760
atttttgtga tgctcgtcag gggggcggag cctatggaaa aacgccagca acgcggcctt   2820
tttacggttc ctggcctttt gctggccttt tgctcacatg ttctttcctg cgttatcccc   2880
tgattctgtg gataaccgta ttaccgcctt tgagtgagct gataccgctc gccgcagccg   2940
aacgaccgag cgcagcgagt cagtgagcga ggaagcggaa gagcgcctga tgcggtattt   3000
tctccttacg catctgtgcg gtatttcaca ccgcatatgg tgcactctca gtacaatctg   3060
ctctgatgcc gcatagttaa gccagtatac actccgctat cgctacgtga ctgggtcatg   3120
gctgcgcccc gacacccgcc aacacccgct gacgcgccct gacgggcttg tctgctcccg   3180
gcatccgctt acagacaagc tgtgaccgtc tccgggagct gcatgtgtca gaggttttca   3240
ccgtcatcac cgaaacgcgc gaggcagggt gccttgatgt gggcgccggc ggtcgagtgg   3300
cgacggcgcg gcttgtccgc gccctggtag attgcctggc cgtaggccag ccattttga    3360
gcggccagcg gccgcgatag gccgacgcga agcgcgggg cgtagggagc gcagcgaccg    3420
aagggtaggc gcttttttgca gctcttcggc tgtgcgctgg ccagacagtt atgcacaggc   3480
caggcgggtt ttaagagttt taataagttt taaagagttt taggcggaaa aatcgccttt   3540
tttctctttt atatcagtca cttacatgtg tgaccggttc ccaatgtacg ctttgggtt    3600
cccaatgtac gggttccggt tcccaatgta cggctttggg ttcccaatgt acgtgctatc   3660
cacaggaaag agacctttc gacctttttc ccctgctagg gcaatttgcc ctagcatctg    3720
ctccgtacat taggaaccgg cggatgcttc gccctcgatc aggttgcggt agcgcatgac   3780
taggatcggg ccagcctgcc ccgcctcctc cttcaaatcg tactccggca ggtcatttga   3840
cccgatcagc ttgcgcacgg tgaaacagaa cttcttgaac tctccggcgc tgccactgcg   3900
ttcgtagatc gtcttgaaca accatctggc ttctgccttg cctgcggcgc ggcgtgccag   3960
gcggtagaga aaacggccga tgccgggatc gatcaaaaag taatcggggt gaaccgtcag   4020
cacgtccggg ttcttgcctt ctgtgatctc gcggtacatc caatcagcta gctcgatctc   4080
gatgtactcc ggccgcccgg tttcgctctt tacgatcttg tagcggctaa tcaaggcttc   4140
accctcggat accgtcacca ggcggccgtt cttggccttc ttcgtacgct gcatggcaac   4200
gtgcgtggtg tttaaccgaa tgcaggtttc taccaggtcg tctttctgct ttccgccatc   4260
ggctcgccgg cagaacttga gtacgtccgc aacgtgtgga cggaacacgc ggccgggctt   4320
gtctcccttc ccttcccggt atcggttcat ggattcggtt agatgggaaa ccgccatcag   4380
taccaggtcg taatcccaca cactggccat gccggccggc cctgcggaaa cctctacgtg   4440
cccgtctgga agctcgtagc ggatcacctc gccagctcgt cggtcacgct tcgacagacg   4500
gaaaacggcc acgtccatga tgctgcgact atcgcgggtg cccacgtcat agagcatcgg   4560
aacgaaaaaa tctggttgct cgtcgccctt gggcggcttc ctaatcgacg gcgcaccggc   4620
tgccggcggt tgccgggatt cttttgcggat tcgatcagcg gccgcttgcc acgattcacc   4680
ggggcgtgct tctgcctcga tgcgttgccg ctgggcggcc tgcgcggcct tcaacttctc   4740
```

```
caccaggtca tcacccagcg ccgcgccgat ttgtaccggg ccggatggtt tgcgaccgtc   4800
acgccgattc ctcgggcttg ggggttccag tgccattgca gggccggcag acaacccagc   4860
cgcttacgcc tggccaaccg cccgttcctc cacacatggg gcattccacg gcgtcggtgc   4920
ctggttgttc ttgatttccc atgccgcctc ctttagccgc taaaattcat ctactcattt   4980
attcatttgc tcatttactc tggtagctgc gcgatgtatt cagatagcag ctcggtaatg   5040
gtcttgcctt ggcgtaccgc gtacatcttc agcttggtgt gatcctccgc cggcaactga   5100
aagttgaccc gcttcatggc tggcgtgtct gccaggctgg ccaacgttgc agccttgctg   5160
ctgcgtgcgc tcggacggcc ggcacttagc gtgtttgtgc ttttgctcat tttctcttta   5220
cctcattaac tcaaatgagt tttgatttaa tttcagcggc cagcgcctgg acctcgcggg   5280
cagcgtcgcc ctcgggttct gattcaagaa cggttgtgcc ggcggcggca gtgcctgggt   5340
agctcacgcg ctgcgtgata cgggactcaa gaatgggcag ctcgtacccg ccagcgcct   5400 cggcaacctc accgccgatg cgcgtgcctt tgatcgcccg cgacacgaca aaggccgctt   5460
gtagccttcc atccgtgacc tcaatgcgct gcttaaccag ctccaccagg tcggcggtgg   5520
cccatatgtc gtaagggctt ggctgcaccg gaatcagcac gaagtcggct gccttgatcg   5580
cggacacagc caagtccgcc gcctgggcg ctccgtcgat cactacgaag tcgcgccggc   5640
cgatggcctt cacgtcgcgg tcaatcgtcg ggcggtcgat gccgacaacg gttagcggtt   5700
gatcttcccg cacggccgcc aatcgcggg cactgccctg gggatcggaa tcgactaaca   5760
gaacatcggc cccggcgagt gcagggcgc gggctagatg ggttgcgatg gtcgtcttgc   5820
ctgacccgcc tttctggtta agtacagcga taaccttcat gcgttcccct gcgtatttg   5880 tttatttact catcgcatca tatacgcagc gaccgcatga cgcaagctgt tttactcaaa   5940
tacacatcac cttttagac ggcggcgctc ggtttcttca gcggccaagc tggccggcca   6000
ggccgccagc ttggcatcag acaaaccggc caggatttca tgcagccgca cggttgagac   6060
gtgcgcgggg ggctcgaaca cgtacccggc cgcgatcatc tccgcctcga tctcttcggt   6120
aatgaaaaac ggttcgtcct ggccgtcctg gtgcggtttc atgcttgttc ctcttggcgt   6180
tcattctcgg cggccgccag ggcgtcggcc tcggtcaatg cgtcctcacg gaaggcaccg   6240
cgccgcctgg cctcggtggg cgtcacttcc tcgctgcgct caagtgcgcg gtacagggtc   6300
gagcgatgca cgccaagcag tgcagccgcc tctttcacgg tgcggccttc ctggtcgatc   6360
agctcgcggg cgtgcgcgat ctgtgccggg gtgagggtag ggcgggggcc aaacttcacg   6420
cctcgggcct tggcggcctc gcgcccgctc cgggtgcgt cgatgattag ggaacgctcg   6480
aactcggcaa tgccggcgaa cacggtcaac accatgcggc cggccggcgt ggtggtgtcg   6540 gcccacgget ctgccaggct acgcaggccc gcgccggcct cctggatgcg ctcggcaatg   6600
tccagtaggt cgcgggtgct gcgggccagg cggtctagcc tggtcactgt cacaacgtcg   6660
ccagggcgta ggtggtcaag catcctggcc agctccgggc ggtcgcgcct ggtgccggtg   6720
atcttctcgg aaaacagctt ggtgcagccg gccgcgtgca gttcggcccg ttggttggtc   6780
aagtcctggt cgtcggtgct gacgcgggca tagcccagca ggccagcggc ggcgctcttg   6840
ttcatggcgt aatgtctccg gttctagtcg caagtattct actttatgcg actaaaacac   6900
gcgacaagaa aacgccagga aaagggcagg gcggcagcct gtcgcgtaac ttaggacttg   6960
tgcgacatgt cgttttcaga agacggctgc actgaacgtc agaagccgac tgcactatag   7020
cagcggaggg gttggatcaa agtactttga tcccgagggg aaccctgtgg ttggcatgca   7080
catacaaatg gacgaacgga taaacctttt cacgccctt taaatatccg ttattctaat   7140
```

```
aaacgctctt ttctcttagg tttacccgcc aatatatcct gtcaaacact gatagtttaa    7200
actgaaggcg ggaaacgaca atctgatcca agctcaagct gctctagcat tcgccattca    7260
ggctgcgcaa ctgttgggaa gggcgatcgg tgcgggcctc ttcgctatta cgccagctgg    7320
cgaaaggggg atgtgctgca aggcgattaa gttgggtaac gccagggttt tcccagtcac    7380
gacgttgtaa aacgacggcc agtgccaagc ttctgcaggt ccgattgaga cttttcaaca    7440
aagggtaata tccggaaacc tcctcggatt ccattgccca gctatctgtc actttattgt    7500
gaagatagtg gaaaggaag gtggctccta caaatgccat cattgcgata aggaaaggc    7560 catcgttgaa gatgcctctg ccgacagtgg tcccaaagat ggaccccac ccacgaggag    7620 catcgtggaa aaagaagacg ttccaaccac gtcttcaaag caagtggatt gatgtgatgg    7680
tccgattgag acttttcaac aaagggtaat atccggaaac ctcctcggat tccattgccc    7740
agctatctgt cactttattg tgaagatagt ggaaaaggaa ggtggctcct acaaatgcca    7800
tcattgcgat aaaggaaagg ccatcgttga agatgcctct gccgacagtg gtcccaaaga    7860
tggaccccca cccacgagga gcatcgtgga aaaagaagac gttccaacca cgtcttcaaa    7920
gcaagtggat tgatgtgata tctccactga cgtaagggat gacgcacaat cccactatcc    7980
ttcgcaagac ccttcctcta tataaggaag ttcatttcat ttggagagga cacgctgaca    8040
agctgactct agcagatcta ccgtcttcgg tacgcgctca ctccgccctc tgcctttgtt    8100
actgccacgt ttctctgaat gctctcttgt gtggtgattg ctgagagtgg tttagctgga    8160
tctagaatta cactctgaaa tcgtgttctg cctgtgctga ttacttgccg tcctttgtag    8220
cagcaaaata tagggacatg gtagtacgaa acgaagatag aacctacaca gcaatacgag    8280
aaatgtgtaa tttggtgctt agcggtattt atttaagcac atgttggtgt tatagggcac    8340
ttggattcag aagtttgctg ttaatttagg cacaggcttc atactacatg ggtcaatagt    8400
atagggattc atattatagg cgatactata ataatttgtt cgtctgcaga gcttattatt    8460
tgccaaaatt agatattcct attctgtttt tgtttgtgtg ctgttaaatt gttaacgcct    8520
gaaggaataa atataaatga cgaaattttg atgtttatct ctgctccttt attgtgacca    8580
taagtcaaga tcagatgcac ttgttttaaa tattgttgtc tgaagaaata agtactgaca    8640
gtattttgat gcattgatct gcttgtttgt tgtaacaaaa tttaaaaata aagagtttcc    8700 ttttttgttgc tctccttacc tcctgatggt atctagtatc taccaactga cactatattg    8760
cttctcttta catacgtatc ttgctcgatg ccttctccct agtgttgacc agtgttactc    8820
acatagtctt tgctcatttc attgtaatgc agataccaag cggcctctag ag    8872
```

<210> SEQ ID NO 2
<211> LENGTH: 23
<212> TYPE: DNA
<213> ORGANISM: artificial sequence
<220> FEATURE:
<223> OTHER INFORMATION: Synthetic oligonucleotide primer

<400> SEQUENCE: 2
caccgattcc caagccctta tta          23

<210> SEQ ID NO 3
<211> LENGTH: 22
<212> TYPE: DNA
<213> ORGANISM: Artificial Sequence
<220> FEATURE:
<223> OTHER INFORMATION: Synthetic oligonucelotide primer.

<400> SEQUENCE: 3
gctttatggg cgagggttgc tg                                          22

<210> SEQ ID NO 4
<211> LENGTH: 264
<212> TYPE: PRT
<213> ORGANISM: Streptomyces kanamyceticus

<400> SEQUENCE: 4

Met Ala Lys Met Arg Ile Ser Pro Glu Leu Lys Lys Leu Ile Glu Lys
1               5                   10                  15

Tyr Arg Cys Val Lys Asp Thr Glu Gly Met Ser Pro Ala Lys Val Tyr
            20                  25                  30

Lys Leu Val Gly Glu Asn Glu Asn Leu Tyr Leu Lys Met Thr Asp Ser
        35                  40                  45

Arg Tyr Lys Gly Thr Thr Tyr Asp Val Glu Arg Glu Lys Asp Met Met
    50                  55                  60

Leu Trp Leu Glu Gly Lys Leu Pro Val Pro Lys Val Leu His Phe Glu
65                  70                  75                  80

Arg His Asp Gly Trp Ser Asn Leu Leu Met Ser Glu Ala Asp Gly Val
                85                  90                  95

Leu Cys Ser Glu Glu Tyr Glu Asp Glu Gln Ser Pro Glu Lys Ile Ile
            100                 105                 110

Glu Leu Tyr Ala Glu Cys Ile Arg Leu Phe His Ser Ile Asp Ile Ser
        115                 120                 125

Asp Cys Pro Tyr Thr Asn Ser Leu Asp Ser Arg Leu Ala Glu Leu Asp
    130                 135                 140

Tyr Leu Leu Asn Asn Asp Leu Ala Asp Val Asp Cys Glu Asn Trp Glu
145                 150                 155                 160

Glu Asp Thr Pro Phe Lys Asp Pro Arg Glu Leu Tyr Asp Phe Leu Lys
                165                 170                 175

Thr Glu Lys Pro Glu Glu Glu Leu Val Phe Ser His Gly Asp Leu Gly
            180                 185                 190

Asp Ser Asn Ile Phe Val Lys Asp Gly Lys Val Ser Gly Phe Ile Asp
        195                 200                 205

Leu Gly Arg Ser Gly Arg Ala Asp Lys Trp Tyr Asp Ile Ala Phe Cys
    210                 215                 220

Val Arg Ser Ile Arg Glu Asp Ile Gly Glu Glu Gln Tyr Val Glu Leu
225                 230                 235                 240

Phe Phe Asp Leu Leu Gly Ile Lys Pro Asp Trp Glu Lys Ile Lys Tyr
                245                 250                 255

Tyr Ile Leu Leu Asp Glu Leu Phe
            260